(12) United States Patent
Mannheimer et al.

(10) Patent No.: US 8,346,328 B2
(45) Date of Patent: Jan. 1, 2013

(54) MEDICAL SENSOR AND TECHNIQUE FOR USING THE SAME

(75) Inventors: Paul D. Mannheimer, Danville, CA (US); Bruce R. Bowman, Eden Prairie, MN (US); Lee M. Middleman, Portola Valley, CA (US); Clark R. Baker, Jr., Newman, CA (US)

(73) Assignee: Covidien LP, Mansfield, MA (US)

( * ) Notice: Subject to any disclaimer, the term of this patent is extended or adjusted under 35 U.S.C. 154(b) by 1410 days.

(21) Appl. No.: 12/004,816

(22) Filed: Dec. 21, 2007
(Under 37 CFR 1.47)

(65) Prior Publication Data
US 2009/0163783 A1  Jun. 25, 2009

(51) Int. Cl.
*A61B 5/1455* (2006.01)

(52) U.S. Cl. ......................... 600/310; 600/322

(58) Field of Classification Search ........... 600/309–344
See application file for complete search history.

(56) References Cited

U.S. PATENT DOCUMENTS

| | | |
|---|---|---|
| 3,403,555 A | 10/1968 | Versaci et al. |
| 3,536,545 A | 10/1970 | Traynor et al. |
| D222,454 S | 10/1971 | Beeber |
| 3,721,813 A | 3/1973 | Condon et al. |
| 4,098,772 A | 7/1978 | Bonk et al. |
| D250,275 S | 11/1978 | Bond |
| D251,387 S | 3/1979 | Ramsay et al. |
| D262,488 S | 12/1981 | Rossman et al. |
| 4,334,544 A | 6/1982 | Hill et al. |
| 4,350,165 A | 9/1982 | Striese |
| 4,353,372 A | 10/1982 | Ayer |
| 4,380,240 A | 4/1983 | Jobsis et al. |
| 4,406,289 A | 9/1983 | Wesseling et al. |
| 4,510,551 A | 4/1985 | Brainard, II |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,677,528 A | 6/1987 | Miniet |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |

(Continued)

FOREIGN PATENT DOCUMENTS

DE  34/05444  8/1985

(Continued)

OTHER PUBLICATIONS

U.S. Appl. No. 11/507,814, filed Aug. 22, 2006, Baker et al.
U.S. Appl. No. 11/525,396, filed Sep. 22, 2006, Hoarau.
U.S. Appl. No. 11/525,693, filed Sep. 22, 2006, Hoarau.
U.S. Appl. No. 11/525,635, filed Sep. 22, 2006, Hoarau.

(Continued)

*Primary Examiner* — Eric Winakur
*Assistant Examiner* — Marjan Fardanesh
(74) *Attorney, Agent, or Firm* — Fletcher Yoder

(57) ABSTRACT

Embodiments disclosed may include a sensor which may be adapted to provide information related to its position on a patient's tissue. A sensor may be provided with tissue contact sensors which may relay a signal related to the sensor's proper placement adjacent a patient's tissue. Such a sensor may be useful for providing information to a clinician about the status of a sensor, such as if a sensor may be located more closely to the tissue in order to provide improved measurements.

18 Claims, 8 Drawing Sheets

U.S. PATENT DOCUMENTS

| | | | |
|---|---|---|---|
| 4,714,341 A | 12/1987 | Hamaguri et al. | |
| 4,722,120 A | 2/1988 | Lu | |
| 4,726,382 A | 2/1988 | Boehmer et al. | |
| 4,759,369 A | 7/1988 | Taylor | |
| 4,770,179 A | 9/1988 | New, Jr. et al. | |
| 4,773,422 A | 9/1988 | Isaacson et al. | |
| 4,776,339 A | 10/1988 | Schreiber | |
| 4,781,195 A | 11/1988 | Martin | |
| 4,783,815 A | 11/1988 | Buttner | |
| 4,796,636 A | 1/1989 | Branstetter et al. | |
| 4,800,495 A | 1/1989 | Smith | |
| 4,800,885 A | 1/1989 | Johnson | |
| 4,802,486 A | 2/1989 | Goodman et al. | |
| 4,805,623 A | 2/1989 | Jöbsis | |
| 4,807,630 A | 2/1989 | Malinouskas | |
| 4,807,631 A | 2/1989 | Hersh et al. | |
| 4,819,646 A | 4/1989 | Cheung et al. | |
| 4,819,752 A | 4/1989 | Zelin | |
| 4,824,242 A | 4/1989 | Frick et al. | |
| 4,825,872 A | 5/1989 | Tan et al. | |
| 4,825,879 A | 5/1989 | Tan et al. | |
| 4,830,014 A | 5/1989 | Goodman et al. | |
| 4,832,484 A | 5/1989 | Aoyagi et al. | |
| 4,846,183 A | 7/1989 | Martin | |
| 4,848,901 A | 7/1989 | Hood, Jr. | |
| 4,854,699 A | 8/1989 | Edgar, Jr. | |
| 4,859,056 A | 8/1989 | Prosser et al. | |
| 4,859,057 A | 8/1989 | Taylor et al. | |
| 4,863,265 A | 9/1989 | Flower et al. | |
| 4,865,038 A | 9/1989 | Rich et al. | |
| 4,867,557 A | 9/1989 | Takatani et al. | |
| 4,869,253 A | 9/1989 | Craig, Jr. et al. | |
| 4,869,254 A | 9/1989 | Stone et al. | |
| 4,880,304 A | 11/1989 | Jaeb et al. | |
| 4,883,055 A | 11/1989 | Merrick | |
| 4,883,353 A | 11/1989 | Hansmann et al. | |
| 4,890,619 A | 1/1990 | Hatschek | |
| 4,892,101 A | 1/1990 | Cheung et al. | |
| 4,901,238 A | 2/1990 | Suzuki et al. | |
| 4,908,762 A | 3/1990 | Suzuki et al. | |
| 4,911,167 A | 3/1990 | Corenman et al. | |
| 4,913,150 A | 4/1990 | Cheung et al. | |
| 4,926,867 A | 5/1990 | Kanda et al. | |
| 4,927,264 A | 5/1990 | Shiga et al. | |
| 4,928,692 A | 5/1990 | Goodman et al. | |
| 4,934,372 A | 6/1990 | Corenman et al. | |
| 4,938,218 A | 7/1990 | Goodman et al. | |
| 4,942,877 A | 7/1990 | Sakai et al. | |
| 4,948,248 A | 8/1990 | Lehman | |
| 4,955,379 A | 9/1990 | Hall | |
| 4,960,126 A | 10/1990 | Conlon et al. | |
| 4,964,408 A | 10/1990 | Hink et al. | |
| 4,971,062 A | 11/1990 | Hasebe et al. | |
| 4,974,591 A | 12/1990 | Awazu et al. | |
| 5,007,423 A | 4/1991 | Branstetter et al. | |
| 5,025,791 A | 6/1991 | Niwa | |
| RE33,643 E | 7/1991 | Isaacson et al. | |
| 5,028,787 A | 7/1991 | Rosenthal et al. | |
| 5,035,243 A | 7/1991 | Muz | |
| 5,040,039 A | 8/1991 | Schmitt et al. | |
| 5,041,187 A | 8/1991 | Hink et al. | |
| 5,054,488 A | 10/1991 | Muz | |
| 5,055,671 A | 10/1991 | Jones | |
| 5,058,588 A | 10/1991 | Kaestle | |
| 5,065,749 A | 11/1991 | Hasebe et al. | |
| 5,066,859 A | 11/1991 | Karkar et al. | |
| 5,069,213 A | 12/1991 | Polczynski | |
| 5,078,136 A | 1/1992 | Stone et al. | |
| 5,086,229 A | 2/1992 | Rosenthal et al. | |
| 5,088,493 A | 2/1992 | Giannini et al. | |
| 5,090,410 A | 2/1992 | Saper et al. | |
| 5,094,239 A | 3/1992 | Jaeb et al. | |
| 5,094,240 A | 3/1992 | Muz | |
| 5,099,841 A | 3/1992 | Heinonen et al. | |
| 5,099,842 A | 3/1992 | Mannheimer et al. | |
| H1039 H | 4/1992 | Tripp, Jr. et al. | |
| 5,104,623 A | 4/1992 | Miller | |
| 5,109,849 A | 5/1992 | Goodman et al. | |
| 5,111,817 A | 5/1992 | Clark et al. | |
| 5,113,861 A | 5/1992 | Rother | |
| D326,715 S | 6/1992 | Schmidt | |
| 5,119,463 A * | 6/1992 | Vurek et al. | 385/129 |
| 5,125,403 A | 6/1992 | Culp | |
| 5,127,406 A | 7/1992 | Yamaguchi | |
| 5,131,391 A | 7/1992 | Sakai et al. | |
| 5,140,989 A | 8/1992 | Lewis et al. | |
| 5,152,296 A | 10/1992 | Simons | |
| 5,154,175 A | 10/1992 | Gunther | |
| 5,158,082 A | 10/1992 | Jones | |
| 5,170,786 A | 12/1992 | Thomas et al. | |
| 5,188,108 A | 2/1993 | Secker et al. | |
| 5,190,038 A | 3/1993 | Polson et al. | |
| 5,193,542 A | 3/1993 | Missanelli et al. | |
| 5,193,543 A | 3/1993 | Yelderman | |
| 5,203,329 A | 4/1993 | Takatani et al. | |
| 5,209,230 A | 5/1993 | Swedlow et al. | |
| 5,213,099 A | 5/1993 | Tripp et al. | |
| 5,216,598 A | 6/1993 | Branstetter et al. | |
| 5,217,012 A | 6/1993 | Young et al. | |
| 5,217,013 A | 6/1993 | Lewis et al. | |
| 5,218,207 A | 6/1993 | Rosenthal | |
| 5,218,962 A | 6/1993 | Mannheimer et al. | |
| 5,224,478 A | 7/1993 | Sakai et al. | |
| 5,226,417 A | 7/1993 | Swedlow et al. | |
| 5,228,440 A | 7/1993 | Chung et al. | |
| 5,237,994 A | 8/1993 | Goldberger | |
| 5,239,185 A | 8/1993 | Ito et al. | |
| 5,246,002 A | 9/1993 | Prosser | |
| 5,246,003 A | 9/1993 | DeLonzor | |
| 5,247,931 A | 9/1993 | Norwood | |
| 5,247,932 A | 9/1993 | Chung et al. | |
| 5,249,576 A | 10/1993 | Goldberger et al. | |
| 5,253,645 A | 10/1993 | Friedman et al. | |
| 5,253,646 A | 10/1993 | Delpy et al. | |
| 5,259,381 A | 11/1993 | Cheung et al. | |
| 5,259,761 A | 11/1993 | Schnettler et al. | |
| 5,263,244 A | 11/1993 | Centa et al. | |
| 5,267,562 A | 12/1993 | Ukawa et al. | |
| 5,267,563 A | 12/1993 | Swedlow et al. | |
| 5,267,566 A | 12/1993 | Choucair et al. | |
| 5,273,036 A | 12/1993 | Kronberg et al. | |
| 5,275,159 A | 1/1994 | Griebel | |
| 5,278,627 A | 1/1994 | Aoyagi et al. | |
| 5,279,295 A | 1/1994 | Martens et al. | |
| 5,285,783 A | 2/1994 | Secker | |
| 5,285,784 A | 2/1994 | Seeker | |
| 5,287,853 A | 2/1994 | Vester et al. | |
| 5,291,884 A | 3/1994 | Heinemann et al. | |
| 5,297,548 A | 3/1994 | Pologe | |
| 5,299,120 A | 3/1994 | Kaestle | |
| 5,299,570 A | 4/1994 | Hatschek | |
| 5,309,908 A | 5/1994 | Friedman et al. | |
| 5,311,865 A | 5/1994 | Mayeux | |
| 5,313,940 A | 5/1994 | Fuse et al. | |
| 5,323,776 A | 6/1994 | Blakeley et al. | |
| 5,329,922 A | 7/1994 | Atlee, III | |
| 5,337,744 A | 8/1994 | Branigan | |
| 5,339,810 A | 8/1994 | Ivers et al. | |
| 5,343,818 A | 9/1994 | McCarthy et al. | |
| 5,343,869 A | 9/1994 | Pross et al. | |
| 5,348,003 A | 9/1994 | Caro | |
| 5,348,004 A | 9/1994 | Hollub et al. | |
| 5,348,005 A | 9/1994 | Merrick et al. | |
| 5,349,519 A | 9/1994 | Kaestle | |
| 5,349,952 A | 9/1994 | McCarthy et al. | |
| 5,349,953 A | 9/1994 | McCarthy et al. | |
| 5,351,685 A | 10/1994 | Potratz | |
| 5,353,799 A | 10/1994 | Chance | |
| 5,355,880 A | 10/1994 | Thomas et al. | |
| 5,355,882 A | 10/1994 | Ukawa et al. | |
| 5,361,758 A | 11/1994 | Hall et al. | |
| 5,365,066 A | 11/1994 | Krueger, Jr. et al. | |
| 5,368,025 A | 11/1994 | Young et al. | |
| 5,368,026 A | 11/1994 | Swedlow et al. | |
| 5,368,224 A | 11/1994 | Richardson et al. | |
| 5,372,136 A | 12/1994 | Steuer et al. | |
| 5,377,675 A | 1/1995 | Ruskewicz et al. | |

| Patent No. | Date | Inventor |
|---|---|---|
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,402,779 A | 4/1995 | Chen et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,043 A | 2/1996 | O'Sullivan et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,991 A | 4/1997 | Guthrie et al. |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,816 A | 6/1997 | Kiani-Azarbayjany et al. |
| 5,638,818 A | 6/1997 | Diab et al. |
| 5,645,060 A | 7/1997 | Yorkey |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,664,270 A | 9/1997 | Bell et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,788,634 A | 8/1998 | Suda et al. |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,179 A | 10/1998 | Lichter et al. |
| 5,827,182 A | 10/1998 | Raley et al. |
| 5,829,439 A | 11/1998 | Yokosawa et al. |
| 5,830,135 A | 11/1998 | Bosque et al. |
| 5,830,136 A | 11/1998 | DeLonzor et al. |
| 5,830,137 A | 11/1998 | Scharf |
| 5,839,439 A | 11/1998 | Nierlich et al. |

| | | | | | | |
|---|---|---|---|---|---|---|
| RE36,000 E | 12/1998 | Swedlow et al. | | 6,073,038 A | 6/2000 | Wang et al. |
| 5,842,979 A | 12/1998 | Jarman et al. | | 6,078,829 A | 6/2000 | Uchida |
| 5,842,981 A | 12/1998 | Larsen et al. | | 6,078,833 A | 6/2000 | Hueber |
| 5,842,982 A | 12/1998 | Mannheimer | | 6,081,735 A | 6/2000 | Diab et al. |
| 5,846,190 A | 12/1998 | Woehrle | | 6,083,157 A | 7/2000 | Noller |
| 5,851,178 A | 12/1998 | Aronow | | 6,083,172 A | 7/2000 | Baker, Jr. et al. |
| 5,851,179 A | 12/1998 | Ritson et al. | | 6,088,607 A | 7/2000 | Diab et al. |
| 5,853,364 A | 12/1998 | Baker, Jr. et al. | | 6,094,592 A | 7/2000 | Yorkey et al. |
| 5,860,919 A | 1/1999 | Kiani-Azarbayjany et al. | | 6,095,974 A | 8/2000 | Shemwell et al. |
| 5,865,736 A | 2/1999 | Baker, Jr. et al. | | 6,104,938 A | 8/2000 | Huiku et al. |
| 5,879,294 A | 3/1999 | Anderson et al. | | 6,104,939 A | 8/2000 | Groner |
| 5,885,213 A | 3/1999 | Richardson et al. | | 6,112,107 A | 8/2000 | Hannula |
| 5,890,929 A | 4/1999 | Mills et al. | | 6,113,541 A | 9/2000 | Dias et al. |
| 5,891,021 A | 4/1999 | Dillon et al. | | 6,115,621 A | 9/2000 | Chin |
| 5,891,022 A | 4/1999 | Pologe | | 6,122,535 A | 9/2000 | Kaestle et al. |
| 5,891,024 A | 4/1999 | Jarman et al. | | 6,133,994 A | 10/2000 | Mathews et al. |
| 5,891,025 A | 4/1999 | Buschmann et al. | | 6,135,952 A | 10/2000 | Coetzee |
| 5,891,026 A | 4/1999 | Wang et al. | | 6,144,444 A | 11/2000 | Haworth et al. |
| 5,902,235 A | 5/1999 | Lewis et al. | | 6,144,867 A | 11/2000 | Walker et al. |
| 5,910,108 A | 6/1999 | Solenberger | | 6,144,868 A | 11/2000 | Parker |
| 5,911,690 A | 6/1999 | Rall | | 6,149,481 A | 11/2000 | Wang et al. |
| 5,912,656 A | 6/1999 | Tham et al. | | 6,151,107 A | 11/2000 | Schöllermann et al. |
| 5,913,819 A | 6/1999 | Taylor et al. | | 6,151,516 A | 11/2000 | Kiani-Azarbayjany et al. |
| 5,916,154 A | 6/1999 | Hobbs et al. | | 6,151,518 A | 11/2000 | Hayashi |
| 5,916,155 A | 6/1999 | Levinson et al. | | 6,152,754 A | 11/2000 | Gerhardt et al. |
| 5,919,133 A | 7/1999 | Taylor et al. | | 6,154,667 A | 11/2000 | Miura et al. |
| 5,919,134 A | 7/1999 | Diab | | 6,157,850 A | 12/2000 | Diab et al. |
| 5,920,263 A | 7/1999 | Huttenhoff et al. | | 6,159,147 A | 12/2000 | Lichter |
| 5,921,921 A | 7/1999 | Potratz et al. | | 6,163,175 A | 12/2000 | Larsen et al. |
| 5,922,607 A | 7/1999 | Bernreuter | | 6,163,715 A | 12/2000 | Larsen et al. |
| 5,924,979 A | 7/1999 | Swedlow et al. | | 6,165,005 A | 12/2000 | Mills et al. |
| 5,924,980 A | 7/1999 | Coetzee | | 6,173,196 B1 | 1/2001 | Delonzor et al. |
| 5,924,982 A | 7/1999 | Chin | | 6,178,343 B1 | 1/2001 | Bindszus et al. |
| 5,924,985 A | 7/1999 | Jones | | 6,179,159 B1 | 1/2001 | Gurley |
| 5,934,277 A | 8/1999 | Mortz | | 6,181,958 B1 | 1/2001 | Steuer et al. |
| 5,934,925 A | 8/1999 | Tobler et al. | | 6,181,959 B1 | 1/2001 | Schöllermann et al. |
| 5,940,182 A | 8/1999 | Lepper, Jr. et al. | | 6,184,521 B1 | 2/2001 | Coffin, IV et al. |
| 5,954,644 A | 9/1999 | Dettling et al. | | 6,188,470 B1 | 2/2001 | Grace |
| 5,957,840 A | 9/1999 | Terasawa et al. | | 6,192,260 B1 | 2/2001 | Chance |
| 5,960,610 A | 10/1999 | Levinson et al. | | 6,195,575 B1 | 2/2001 | Levinson |
| 5,961,450 A | 10/1999 | Merchant et al. | | 6,198,951 B1 | 3/2001 | Kosuda et al. |
| 5,961,452 A | 10/1999 | Chung et al. | | 6,206,830 B1 | 3/2001 | Diab et al. |
| 5,964,701 A | 10/1999 | Asada et al. | | 6,213,952 B1 | 4/2001 | Finarov et al. |
| 5,971,930 A | 10/1999 | Elghazzawi | | 6,217,523 B1 | 4/2001 | Amano et al. |
| 5,978,691 A | 11/1999 | Mills | | 6,222,189 B1 | 4/2001 | Misner et al. |
| 5,978,693 A | 11/1999 | Hamilton et al. | | 6,223,064 B1 | 4/2001 | Lynn |
| 5,983,120 A | 11/1999 | Groner et al. | | 6,226,539 B1 | 5/2001 | Potratz |
| 5,983,122 A | 11/1999 | Jarman et al. | | 6,226,540 B1 | 5/2001 | Bernreuter et al. |
| 5,987,343 A | 11/1999 | Kinast | | 6,229,856 B1 | 5/2001 | Diab et al. |
| 5,991,648 A | 11/1999 | Levin | | 6,230,035 B1 | 5/2001 | Aoyagi et al. |
| 5,995,855 A | 11/1999 | Kiani et al. | | 6,233,470 B1 | 5/2001 | Tsuchiya |
| 5,995,856 A | 11/1999 | Mannheimer et al. | | 6,236,871 B1 | 5/2001 | Tsuchiya |
| 5,995,858 A | 11/1999 | Kinast | | 6,236,872 B1 | 5/2001 | Diab et al. |
| 5,995,859 A | 11/1999 | Takahashi | | 6,240,305 B1 | 5/2001 | Tsuchiya |
| 5,997,343 A | 12/1999 | Mills et al. | | 6,253,097 B1 | 6/2001 | Aronow et al. |
| 5,999,834 A | 12/1999 | Wang et al. | | 6,253,098 B1 | 6/2001 | Walker et al. |
| 6,002,952 A | 12/1999 | Diab et al. | | 6,256,523 B1 | 7/2001 | Diab et al. |
| 6,005,658 A | 12/1999 | Kaluza et al. | | 6,256,524 B1 | 7/2001 | Walker et al. |
| 6,006,120 A | 12/1999 | Levin | | 6,261,236 B1 | 7/2001 | Grinblatov |
| 6,011,985 A | 1/2000 | Athan et al. | | 6,263,221 B1 | 7/2001 | Chance et al. |
| 6,011,986 A | 1/2000 | Diab et al. | | 6,263,222 B1 | 7/2001 | Diab et al. |
| 6,014,576 A | 1/2000 | Raley et al. | | 6,263,223 B1 | 7/2001 | Sheperd et al. |
| 6,018,673 A | 1/2000 | Chin et al. | | 6,266,546 B1 | 7/2001 | Steuer et al. |
| 6,018,674 A | 1/2000 | Aronow | | 6,266,547 B1 | 7/2001 | Walker et al. |
| 6,022,321 A | 2/2000 | Amano et al. | | 6,272,363 B1 | 8/2001 | Casciani et al. |
| 6,023,541 A | 2/2000 | Merchant et al. | | 6,278,522 B1 | 8/2001 | Lepper, Jr. et al. |
| 6,026,312 A | 2/2000 | Shemwell et al. | | 6,280,213 B1 | 8/2001 | Tobler et al. |
| 6,026,314 A | 2/2000 | Amerov et al. | | 6,280,381 B1 | 8/2001 | Malin et al. |
| 6,031,603 A | 2/2000 | Fine et al. | | 6,285,894 B1 | 9/2001 | Oppelt et al. |
| 6,035,223 A | 3/2000 | Baker, Jr. | | 6,285,895 B1 | 9/2001 | Ristolainen et al. |
| 6,036,642 A | 3/2000 | Diab et al. | | 6,285,896 B1 | 9/2001 | Tobler et al. |
| 6,041,247 A | 3/2000 | Weckstrom et al. | | 6,298,252 B1 | 10/2001 | Kovach et al. |
| 6,044,283 A | 3/2000 | Fein et al. | | 6,308,089 B1 | 10/2001 | Von der Ruhr et al. |
| 6,047,201 A | 4/2000 | Jackson, III | | 6,321,100 B1 | 11/2001 | Parker |
| 6,055,447 A | 4/2000 | Well | | 6,330,468 B1 | 12/2001 | Scharf |
| 6,061,584 A | 5/2000 | Lovejoy et al. | | 6,334,065 B1 | 12/2001 | Al-Ali et al. |
| 6,064,898 A | 5/2000 | Aldrich | | 6,339,715 B1 | 1/2002 | Bahr et al. |
| 6,064,899 A | 5/2000 | Fein et al. | | 6,342,039 B1 | 1/2002 | Lynn |
| 6,067,462 A | 5/2000 | Diab et al. | | 6,343,223 B1 | 1/2002 | Chin et al. |

| | | |
|---|---|---|
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,398,727 B1 | 6/2002 | Bui et al. |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,415,166 B1 | 7/2002 | Van Hoy et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,546,267 B1 | 4/2003 | Sugiura et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,579,242 B2 | 6/2003 | Bui et al. |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,600,940 B1 | 7/2003 | Fein et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura et al. |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,701,170 B2 | 3/2004 | Stetson |
| 6,702,752 B2 | 3/2004 | Dekker |
| 6,707,257 B2 | 3/2004 | Norris |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,762 B1 | 3/2004 | Lichter |
| 6,714,803 B1 | 3/2004 | Mortz |

| | | |
|---|---|---|
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,725,074 B1 | 4/2004 | Kästle |
| 6,725,075 B2 | 4/2004 | Al-Ali |
| 6,731,962 B1 | 5/2004 | Katarow |
| 6,731,963 B2 | 5/2004 | Finarov et al. |
| 6,731,967 B1 | 5/2004 | Turcott |
| 6,735,459 B2 | 5/2004 | Parker |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,754,515 B1 | 6/2004 | Pologe |
| 6,754,516 B2 | 6/2004 | Mannheimer |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | DeLonzor et al. |
| 6,763,256 B2 | 7/2004 | Kimball et al. |
| 6,770,028 B1 | 8/2004 | Ali et al. |
| 6,771,994 B2 | 8/2004 | Kiani et al. |
| 6,773,397 B2 | 8/2004 | Kelly |
| 6,778,923 B2 | 8/2004 | Norris et al. |
| 6,780,158 B2 | 8/2004 | Yarita |
| 6,791,689 B1 | 9/2004 | Weckstrom |
| 6,792,300 B1 | 9/2004 | Diab et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,805,673 B2 | 10/2004 | Dekker |
| 6,810,277 B2 | 10/2004 | Edgar, Jr. et al. |
| 6,813,511 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,825,619 B2 | 11/2004 | Norris |
| 6,826,419 B2 | 11/2004 | Diab et al. |
| 6,829,496 B2 | 12/2004 | Nagai et al. |
| 6,830,549 B2 | 12/2004 | Bui et al. |
| 6,830,711 B2 | 12/2004 | Mills et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,845,256 B2 | 1/2005 | Chin et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,879,850 B2 | 4/2005 | Kimball |
| 6,882,874 B2 | 4/2005 | Huiku |
| 6,898,452 B2 | 5/2005 | Al-Ali et al. |
| 6,909,912 B2 | 6/2005 | Melker et al. |
| 6,912,413 B2 | 6/2005 | Rantala et al. |
| 6,920,345 B2 | 7/2005 | Al-Ali et al. |
| 6,931,269 B2 | 8/2005 | Terry |
| 6,934,570 B2 | 8/2005 | Kiani et al. |
| 6,941,162 B2 | 9/2005 | Fudge et al. |
| 6,947,781 B2 | 9/2005 | Asada et al. |
| 6,950,687 B2 | 9/2005 | Al-Ali |
| 6,954,664 B2 | 10/2005 | Sweitzer |
| 6,968,221 B2 | 11/2005 | Rosenthal |
| 6,979,812 B2 | 12/2005 | Al-Ali |
| 6,983,178 B2 | 1/2006 | Fine et al. |
| 6,985,762 B2 | 1/2006 | Brashears et al. |
| 6,985,763 B2 | 1/2006 | Boas et al. |
| 6,985,764 B2 | 1/2006 | Mason et al. |
| 6,987,994 B1 | 1/2006 | Mortz |
| 6,990,426 B2 | 1/2006 | Yoon et al. |
| 6,992,751 B2 | 1/2006 | Okita et al. |
| 6,992,772 B2 | 1/2006 | Block |
| 6,993,371 B2 | 1/2006 | Kiani et al. |
| 6,993,372 B2 | 1/2006 | Fine et al. |
| 6,996,427 B2 | 2/2006 | Ali et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,020,507 B2 | 3/2006 | Scharf et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali |
| 7,027,850 B2 | 4/2006 | Wasserman |
| 7,039,449 B2 | 5/2006 | Al-Ali |
| 7,039,538 B2 | 5/2006 | Baker |
| 7,043,289 B2 | 5/2006 | Fine et al. |
| 7,047,055 B2 | 5/2006 | Boas et al. |
| 7,060,035 B2 | 6/2006 | Wasserman |
| 7,062,307 B2 | 6/2006 | Norris et al. |
| 7,067,893 B2 | 6/2006 | Mills et al. |
| 7,072,701 B2 | 7/2006 | Chen et al. |
| 7,072,702 B2 | 7/2006 | Edgar, Jr. et al. |
| 7,079,880 B2 | 7/2006 | Stetson |
| 7,085,597 B2 | 8/2006 | Fein et al. |
| 7,096,052 B2 | 8/2006 | Mason et al. |
| 7,096,054 B2 | 8/2006 | Abdul-Hafiz et al. |
| 7,107,088 B2 | 9/2006 | Aceti |
| 7,113,815 B2 | 9/2006 | O'Neil et al. |
| 7,123,950 B2 | 10/2006 | Mannheimer |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,139,559 B2 | 11/2006 | Kenagy et al. |
| 7,142,901 B2 | 11/2006 | Kiani et al. |
| 7,162,288 B2 | 1/2007 | Nordstrom et al. |
| 7,190,987 B2 | 3/2007 | Kindekugel et al. |
| 7,194,293 B2 | 3/2007 | Baker |
| 7,198,778 B2 | 4/2007 | Achilefu et al. |
| 7,209,774 B2 | 4/2007 | Baker |
| 7,215,984 B2 | 5/2007 | Diab et al. |
| 7,225,006 B2 | 5/2007 | Al-Ali et al. |
| 7,228,161 B2 | 6/2007 | Chin |
| 7,236,881 B2 | 6/2007 | Schmitt et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,280,858 B2 | 10/2007 | Al-Ali et al. |
| 7,295,866 B2 | 11/2007 | Al-Ali |
| 7,305,262 B2 | 12/2007 | Brodnick et al. |
| 7,315,753 B2 | 1/2008 | Baker, Jr. et al. |
| 7,389,131 B2 * | 6/2008 | Kanayama ............... 600/322 |
| 7,392,075 B2 | 6/2008 | Baker |
| 7,471,969 B2 | 12/2008 | Diab et al. |
| 7,474,907 B2 | 1/2009 | Baker |
| 7,500,950 B2 | 3/2009 | Al-Ali et al. |
| 2002/0016537 A1 | 2/2002 | Muz et al. |
| 2002/0026109 A1 | 2/2002 | Diab et al. |
| 2002/0028990 A1 | 3/2002 | Shepherd et al. |
| 2002/0038078 A1 | 3/2002 | Ito |
| 2002/0042558 A1 | 4/2002 | Mendelson |
| 2002/0068859 A1 | 6/2002 | Knopp |
| 2002/0072681 A1 | 6/2002 | Schnali |
| 2002/0103423 A1 | 8/2002 | Chin et al. |
| 2002/0116797 A1 | 8/2002 | Modgil et al. |
| 2002/0128544 A1 | 9/2002 | Diab et al. |
| 2002/0133067 A1 | 9/2002 | Jackson, III |
| 2002/0156354 A1 | 10/2002 | Larson |
| 2002/0173706 A1 | 11/2002 | Takatani |
| 2002/0190863 A1 | 12/2002 | Lynn |
| 2003/0018243 A1 | 1/2003 | Gerhardt et al. |
| 2003/0036690 A1 | 2/2003 | Geddes et al. |
| 2003/0045785 A1 | 3/2003 | Diab et al. |
| 2003/0073889 A1 | 4/2003 | Keilbach et al. |

| | | |
|---|---|---|
| 2003/0073890 A1 | 4/2003 | Hanna |
| 2003/0100840 A1 | 5/2003 | Sugiura et al. |
| 2003/0187337 A1 | 10/2003 | Tarassenko et al. |
| 2003/0197679 A1 | 10/2003 | Ali et al. |
| 2003/0212316 A1 | 11/2003 | Leiden et al. |
| 2003/0225323 A1 | 12/2003 | Kiani et al. |
| 2004/0006261 A1 | 1/2004 | Swedlow et al. |
| 2004/0024326 A1 | 2/2004 | Yeo et al. |
| 2004/0039272 A1 | 2/2004 | Abdul-Hafiz et al. |
| 2004/0039273 A1 | 2/2004 | Terry |
| 2004/0054291 A1 | 3/2004 | Schulz et al. |
| 2004/0068164 A1 | 4/2004 | Diab et al. |
| 2004/0092805 A1 | 5/2004 | Yarita |
| 2004/0097797 A1 | 5/2004 | Porges et al. |
| 2004/0098009 A1 | 5/2004 | Boecker et al. |
| 2004/0117891 A1 | 6/2004 | Hannula et al. |
| 2004/0147824 A1 | 7/2004 | Diab et al. |
| 2004/0158134 A1 | 8/2004 | Diab et al. |
| 2004/0162472 A1 | 8/2004 | Berson et al. |
| 2004/0167381 A1 | 8/2004 | Lichter |
| 2004/0186358 A1 | 9/2004 | Chernow et al. |
| 2004/0204637 A1 | 10/2004 | Diab et al. |
| 2004/0204638 A1 | 10/2004 | Diab et al. |
| 2004/0204639 A1 | 10/2004 | Casciani et al. |
| 2004/0204865 A1 | 10/2004 | Lee et al. |
| 2004/0210146 A1 | 10/2004 | Diab et al. |
| 2004/0215085 A1 | 10/2004 | Schnall |
| 2004/0236196 A1 | 11/2004 | Diab et al. |
| 2005/0004479 A1 | 1/2005 | Townsend et al. |
| 2005/0014999 A1 | 1/2005 | Rahe-Meyer |
| 2005/0020887 A1 | 1/2005 | Goldberg |
| 2005/0033131 A1 | 2/2005 | Chen |
| 2005/0043599 A1 | 2/2005 | O'Mara |
| 2005/0043600 A1 | 2/2005 | Diab et al. |
| 2005/0049468 A1 | 3/2005 | Carlson |
| 2005/0070773 A1 | 3/2005 | Chin |
| 2005/0075546 A1 | 4/2005 | Samsoondar |
| 2005/0075548 A1 | 4/2005 | Al-Ali et al. |
| 2005/0075550 A1 | 4/2005 | Lindekugel |
| 2005/0085704 A1 | 4/2005 | Schulz |
| 2005/0090720 A1 | 4/2005 | Wu |
| 2005/0197548 A1 | 9/2005 | Dietiker |
| 2005/0197579 A1 | 9/2005 | Baker |
| 2005/0197793 A1 | 9/2005 | Baker |
| 2005/0228248 A1 | 10/2005 | Dietiker |
| 2005/0250998 A1 | 11/2005 | Huiku |
| 2005/0256386 A1 | 11/2005 | Chan |
| 2005/0272986 A1 | 12/2005 | Smith |
| 2005/0277819 A1 | 12/2005 | Kiani et al. |
| 2006/0020179 A1 | 1/2006 | Anderson |
| 2006/0030764 A1 | 2/2006 | Porges |
| 2006/0058594 A1 | 3/2006 | Ishizuka et al. |
| 2006/0074280 A1 | 4/2006 | Martis |
| 2006/0084852 A1 | 4/2006 | Mason et al. |
| 2006/0084878 A1 | 4/2006 | Banet |
| 2006/0089547 A1 | 4/2006 | Sarussi |
| 2006/0106294 A1 | 5/2006 | Maser et al. |
| 2006/0122476 A1 | 6/2006 | Van Slyke |
| 2006/0122517 A1 | 6/2006 | Banet |
| 2006/0129039 A1 | 6/2006 | Lindner |
| 2006/0155198 A1 | 7/2006 | Schmid |
| 2006/0173257 A1 | 8/2006 | Nagai |
| 2006/0195280 A1 | 8/2006 | Baker |
| 2006/0211925 A1 | 9/2006 | Lamego et al. |
| 2006/0211932 A1 | 9/2006 | Al-Ali et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0220881 A1 | 10/2006 | Al-Ali et al. |
| 2006/0224059 A1 | 10/2006 | Swedlow et al. |
| 2006/0226992 A1 | 10/2006 | Al-Ali et al. |
| 2006/0229510 A1 | 10/2006 | Fein et al. |
| 2006/0229511 A1 | 10/2006 | Fein et al. |
| 2006/0238358 A1 | 10/2006 | Al-Ali et al. |
| 2007/0027376 A1 | 2/2007 | Todokoro et al. |
| 2007/0032710 A1 | 2/2007 | Raridan et al. |
| 2007/0032712 A1 | 2/2007 | Raridan et al. |
| 2007/0032715 A1 | 2/2007 | Eghbal et al. |
| 2007/0043269 A1 | 2/2007 | Mannheimer et al. |
| 2007/0043270 A1 | 2/2007 | Mannheimer et al. |
| 2007/0043271 A1 | 2/2007 | Mannheimer et al. |
| 2007/0043272 A1 | 2/2007 | Mannheimer et al. |
| 2007/0043273 A1 | 2/2007 | Mannheimer et al. |
| 2007/0043274 A1 | 2/2007 | Mannheimer et al. |
| 2007/0043275 A1 | 2/2007 | Manheimer et al. |
| 2007/0043276 A1 | 2/2007 | Mannheimer et al. |
| 2007/0043277 A1 | 2/2007 | Mannheimer et al. |
| 2007/0043278 A1 | 2/2007 | Mannheimer et al. |
| 2007/0043279 A1 | 2/2007 | Mannheimer et al. |
| 2007/0043280 A1 | 2/2007 | Mannheimer et al. |
| 2007/0043282 A1 | 2/2007 | Mannheimer et al. |
| 2007/0049810 A1 | 3/2007 | Mannheimer et al. |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073122 A1 | 3/2007 | Hoarau |
| 2007/0073123 A1 | 3/2007 | Raridan |
| 2007/0073125 A1 | 3/2007 | Hoarau et al. |
| 2007/0073126 A1 | 3/2007 | Raridan |
| 2007/0073128 A1 | 3/2007 | Hoarau |
| 2007/0078315 A1 | 4/2007 | Kling et al. |
| 2007/0078316 A1 | 4/2007 | Hoarau |
| 2007/0088207 A1 | 4/2007 | Mannheimer et al. |
| 2007/0100220 A1 | 5/2007 | Baker et al. |
| 2007/0106137 A1 | 5/2007 | Baker et al. |
| 2007/0129616 A1 | 6/2007 | Rantala |
| 2007/0208240 A1 | 9/2007 | Nordstrom et al. |
| 2007/0225614 A1* | 9/2007 | Naghavi et al. .......... 600/549 |
| 2007/0260129 A1 | 11/2007 | Chin |
| 2007/0260130 A1 | 11/2007 | Chin |
| 2007/0260131 A1 | 11/2007 | Chin |
| 2007/0282478 A1 | 12/2007 | Al-Ali et al. |
| 2007/0299328 A1 | 12/2007 | Chin et al. |
| 2008/0081974 A1 | 4/2008 | Pav |
| 2008/0088467 A1 | 4/2008 | Al-Ali |
| 2008/0097175 A1 | 4/2008 | Boyce et al. |
| 2008/0103375 A1 | 5/2008 | Kiani |
| 2008/0108884 A1 | 5/2008 | Kiani |
| 2008/0183057 A1 | 7/2008 | Taube |
| 2008/0188733 A1 | 8/2008 | Al-Ali et al. |
| 2008/0221418 A1 | 9/2008 | Al-Ali et al. |
| 2008/0255436 A1 | 10/2008 | Baker |
| 2008/0262326 A1 | 10/2008 | Hete et al. |
| 2008/0262328 A1 | 10/2008 | Adams |
| 2008/0287757 A1 | 11/2008 | Berson et al. |

FOREIGN PATENT DOCUMENTS

| | | |
|---|---|---|
| DE | 35/16338 | 11/1986 |
| DE | 37/03458 | 8/1988 |
| DE | 39/38759 | 5/1991 |
| DE | 4210102 | 9/1993 |
| DE | 44/23597 | 8/1995 |
| DE | 19/632361 | 2/1997 |
| DE | 69/123448 | 5/1997 |
| DE | 19/703220 | 7/1997 |
| DE | 19640807 | 9/1997 |
| DE | 19647877 | 4/1998 |
| DE | 10030862 | 1/2002 |
| DE | 20318882 | 4/2004 |
| EP | 0127947 | 5/1984 |
| EP | 00194105 | 9/1986 |
| EP | 00204459 | 12/1986 |
| EP | 02/62779 | 4/1988 |
| EP | 0315040 | 10/1988 |
| EP | 0314331 | 5/1989 |
| EP | 00352923 | 1/1990 |
| EP | 03/60977 | 4/1990 |
| EP | 00430340 | 6/1991 |
| EP | 04/35500 | 7/1991 |
| EP | 0572684 | 5/1992 |
| EP | 00497021 | 8/1992 |
| EP | 0529412 | 8/1992 |
| EP | 0531631 | 9/1992 |
| EP | 0566354 | 4/1993 |
| EP | 0587009 | 8/1993 |
| EP | 00630203 | 9/1993 |

| | | | | | | |
|---|---|---|---|---|---|---|
| EP | 05/72684 | 12/1993 | | JP | 23339678 | 12/2003 |
| EP | 00615723 | 9/1994 | | JP | 24008572 | 1/2004 |
| EP | 00702931 | 3/1996 | | JP | 24089546 | 3/2004 |
| EP | 00724860 | 8/1996 | | JP | 24113353 | 4/2004 |
| EP | 00793942 | 9/1997 | | JP | 24135854 | 5/2004 |
| EP | 08/64293 | 9/1998 | | JP | 24148069 | 5/2004 |
| EP | 01006863 | 10/1998 | | JP | 24148070 | 5/2004 |
| EP | 01006864 | 10/1998 | | JP | 24159810 | 6/2004 |
| EP | 0875199 | 11/1998 | | JP | 24166775 | 6/2004 |
| EP | 00998214 | 12/1998 | | JP | 24194908 | 7/2004 |
| EP | 0/898933 | 3/1999 | | JP | 24202190 | 7/2004 |
| EP | 0898933 | 3/1999 | | JP | 24248819 | 9/2004 |
| EP | 01332713 | 8/2003 | | JP | 24248820 | 9/2004 |
| EP | 01469773 | 8/2003 | | JP | 24261364 | 9/2004 |
| EP | 1502529 | 7/2004 | | JP | 24290412 | 10/2004 |
| EP | 01491135 | 12/2004 | | JP | 24290544 | 10/2004 |
| EP | 1807001 | 7/2007 | | JP | 24290545 | 10/2004 |
| FR | 2685865 | 1/1992 | | JP | 24329406 | 11/2004 |
| GB | 22/59545 | 3/1993 | | JP | 24329607 | 11/2004 |
| JP | 63275325 | 11/1988 | | JP | 24329928 | 11/2004 |
| JP | 2013450 | 1/1990 | | JP | 24337605 | 12/2004 |
| JP | 2111343 | 4/1990 | | JP | 24344367 | 12/2004 |
| JP | 02/191434 | 7/1990 | | JP | 24351107 | 12/2004 |
| JP | 2237544 | 9/1990 | | JP | 25034472 | 2/2005 |
| JP | 03/173536 | 7/1991 | | WO | WO 98/09566 | 10/1989 |
| JP | 3170866 | 7/1991 | | WO | WO 90/01293 | 2/1990 |
| JP | 3245042 | 10/1991 | | WO | WO9001293 | 2/1990 |
| JP | 4174648 | 6/1992 | | WO | WO 90/04352 | 5/1990 |
| JP | 4191642 | 7/1992 | | WO | WO 91/01678 | 2/1991 |
| JP | 4332536 | 11/1992 | | WO | WO 91/11137 | 8/1991 |
| JP | 3124073 | 3/1993 | | WO | WO 92/00513 | 1/1992 |
| JP | 5049624 | 3/1993 | | WO | WO 92/21281 | 12/1992 |
| JP | 5049625 | 3/1993 | | WO | WO 93/09711 | 5/1993 |
| JP | 3115374 | 4/1993 | | WO | WO 93/13706 | 7/1993 |
| JP | 05/200031 | 8/1993 | | WO | WO 93/16629 | 9/1993 |
| JP | 2005/200031 | 8/1993 | | WO | WO 94/03102 | 2/1994 |
| JP | 5212016 | 8/1993 | | WO | WO 94/23643 | 10/1994 |
| JP | 06/014906 | 1/1994 | | WO | WO 95/02358 | 1/1995 |
| JP | 06014906 | 1/1994 | | WO | WO 95/12349 | 5/1995 |
| JP | 6016774 | 3/1994 | | WO | WO 95/16970 | 6/1995 |
| JP | 3116255 | 4/1994 | | WO | WO 96/13208 | 5/1996 |
| JP | 6029504 | 4/1994 | | WO | WO 96/39927 | 12/1996 |
| JP | 6098881 | 4/1994 | | WO | WO 97/36536 | 10/1997 |
| JP | 06/154177 | 6/1994 | | WO | WO 97/36538 | 10/1997 |
| JP | 6269430 | 9/1994 | | WO | WO 97/49330 | 12/1997 |
| JP | 6285048 | 10/1994 | | WO | WO 98/17174 | 4/1998 |
| JP | 7001273 | 1/1995 | | WO | WO 98/18382 | 5/1998 |
| JP | 7124138 | 5/1995 | | WO | WO 98/43071 | 10/1998 |
| JP | 7136150 | 5/1995 | | WO | WO 98/51212 | 11/1998 |
| JP | 3116259 | 6/1995 | | WO | WO 98/57577 | 12/1998 |
| JP | 3116260 | 6/1995 | | WO | WO 99/00053 | 1/1999 |
| JP | 7155311 | 6/1995 | | WO | WO 99/32030 | 7/1999 |
| JP | 7155313 | 6/1995 | | WO | WO 99/47039 | 9/1999 |
| JP | 3238813 | 7/1995 | | WO | WO 99/63884 | 12/1999 |
| JP | 7171139 | 7/1995 | | WO | WO 00/21438 | 4/2000 |
| JP | 3134144 | 9/1995 | | WO | WO 00/28888 | 5/2000 |
| JP | 7236625 | 9/1995 | | WO | WO 00/59374 | 10/2000 |
| JP | 7246191 | 9/1995 | | WO | WO 01/13790 | 3/2001 |
| JP | 8256996 | 10/1996 | | WO | WO 01/16577 | 3/2001 |
| JP | 9192120 | 7/1997 | | WO | WO 01/17421 | 3/2001 |
| JP | 10216113 | 8/1998 | | WO | WO 01/47426 | 3/2001 |
| JP | 10216114 | 8/1998 | | WO | WO 01/40776 | 6/2001 |
| JP | 10216115 | 8/1998 | | WO | WO 01/76461 | 10/2001 |
| JP | 10337282 | 12/1998 | | WO | WO 02/14793 | 2/2002 |
| JP | 11019074 | 1/1999 | | WO | WO 02/35999 | 5/2002 |
| JP | 11155841 | 6/1999 | | WO | WO 02/062213 | 8/2002 |
| JP | 11/188019 | 7/1999 | | WO | WO 02/074162 | 9/2002 |
| JP | 11244268 | 9/1999 | | WO | WO 03/000125 | 1/2003 |
| JP | 20107157 | 4/2000 | | WO | WO 03/001180 | 1/2003 |
| JP | 20237170 | 9/2000 | | WO | WO 03/009750 | 2/2003 |
| JP | 21245871 | 9/2001 | | WO | WO 03/011127 | 2/2003 |
| JP | 22224088 | 8/2002 | | WO | WO 03/039326 | 5/2003 |
| JP | 22282242 | 10/2002 | | WO | WO 03/063697 | 8/2003 |
| JP | 23153881 | 5/2003 | | WO | WO 03/073924 | 9/2003 |
| JP | 23153882 | 5/2003 | | WO | WO 2004/000114 | 12/2003 |
| JP | 23169791 | 6/2003 | | WO | WO 2004/006748 | 1/2004 |
| JP | 23194714 | 7/2003 | | WO | WO 2004/075746 | 9/2004 |
| JP | 23210438 | 7/2003 | | WO | WO 2005/002434 | 1/2005 |
| JP | 23275192 | 9/2003 | | WO | WO 2005/009221 | 2/2005 |

| WO | WO 2005/010567 | 2/2005 |
| WO | WO 2005/010568 | 2/2005 |
| WO | WO 2005/020120 | 3/2005 |
| WO | WO 2005/065540 | 7/2005 |

OTHER PUBLICATIONS

U.S. Appl. No. 11/525,636, filed Sep. 22, 2006, Hoarau.

U.S. Appl. No. 11/525,704, filed Sep. 22, 2006, Hoarau.

U.S. Appl. No. 11/527,762, filed Sep. 26, 2006, Ollerdessen et al.

U.S. Appl. No. 11/716,770, filed Mar. 9, 2007, Hoarau et al.

U.S. Appl. No. 12/005,023, filed Dec. 21, 2007, Bowman et al.

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Zahar, N., et al.; "Automatic Feedback Control of Oxygen Therapy Using Pulse Oximetry, *Annual International Conference of the IEEE Engineering in Medicine and Biology Society*," vol. 13, No. 4, pp. 1614-1615(1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19$^{th}$ International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse OXimetry and PPG Measurements in Plastic Surgery," *Proceedings—19$^{th}$ International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20$^{th}$ annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximeter Sensor with improved Linearity and General Applicability to Various Portions of the Body," *Proceedings of the 20$^{th}$ Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20$^{th}$ Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmographic Sensor," *Proceedings of the First joint BMES/EMBS Conference*, Oct. 13-16, 1999, Altanta, Georgia, p. 786.

Rohling, Roman, et, al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Gobel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28;2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance—Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vo. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 2326, 2002; pp. 1769-1770.

Yamaya, Yoshiki, et al.; "Validity of pulse oximetry during maximal exercise in normoxia, hypoxia, and hyperoxia," *J. Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; Multiple diagnosis based on Photoplethysmography: hematocrib, $Sp_{O2}$, pulse and respiration, *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisarn, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," Toyaku Zasshi (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo (Aritificial Respiration)*, vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Ostmark, Ake, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2/SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2/SPO_2$ Ear Sensor," *Journal of Clinical Monitoring and Computing*, vol. 18, pp. 75-79 (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S., et al.; "Extracting Breathing Rate Infromation from a Wearable Reflectance Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

J. Hayoz, et al.; "World's First Combined digital Pulse Oximetry Pulse Oximetry and Carbon Dioxide Tension Ear Sensor", *Abstracts*, A6, p. S103. (undated).

J. Huang, et al.; "Low Power Motion Tolerant Pulse Oximetry," *Abstracts*, A7, p. S103. (undated).

P. Lang, et al.; "Signal Identification and Quality Indicator™ for Motion Resistant Pulse Oximetry," *Abstracts*, A10, p. S105. (undated).

Hamilton, Patrick S., et al.; "Effect of Adaptive Motion-Artifact Reduction on QRS Detection," *Biomedical Instrumentation & Technology*, pp. 197-202 (undated).

Kim, J.M., et al.; "Signal Processing Using Fourier & Wavelet Transform," pp. II-310-II-311 (undated).

Lee, C.M., et al.; "Reduction of Motion Artifacts from Photoplethysmographic Records Using a Wavelet Denoising Approach," *IEEE*, pp. 194-195 (undated).

Nogawa, Masamichi, et al.; "A New Hybrid Reflectance Optical Pulse Oximetry Sensor for Lower Oxygen Saturation Measurement and for Broader Clinical Application," *SPIE*, vol. 2976, pp. 78-87 (undated).

Odagiri, Y.; "Pulse Wave Measuring Device," *Micromechatronics*, vol. 42, No. 3, pp. 6-11 (undated) (Article in Japanese—contains English summary of article).

Yamazaki, Nakaji, et al.; "Motion Artifact Resistant Pulse Oximeter (Durapulse PA 2100)," *Journal of Oral Cavity Medicine*, vol. 69, No. 4, pp. 53 (date unknown) (Article in Japanese—contains English summary of article).

\* cited by examiner

MEDICAL SENSOR AND TECHNIQUE FOR USING THE SAME

BACKGROUND

The present disclosure relates generally to medical devices and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices may have been developed for monitoring many such physiological characteristics. Such devices may provide doctors and other healthcare personnel with information they may utilize to provide the best possible healthcare for their patients. As a result, such monitoring devices may have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the oxygen saturation of hemoglobin in arterial blood, the volume of individual blood pulsations supplying the tissue, and/or the rate of blood pulsations corresponding to each heartbeat of a patient. The "pulse" in pulse oximetry may refer to the time varying amount of arterial blood in the tissue during each cardiac cycle.

Pulse oximeters may utilize a non-invasive sensor capable of transmitting light through a patient's tissue and that photoelectrically detects the absorption and/or scattering of the transmitted light in such tissue. Physiological characteristics may then be calculated based at least in part upon the amount of light absorbed or scattered. The light passed through the tissue may be typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

To facilitate accurate and reliable measurements when monitoring physiological characteristics of a patient, a pulse oximetry sensor should be adequately in contact with the patient's tissue. When a sensor is dislodged or removed from the patient, or contact is inadequate, some or all of the emitted light does not pass through the patient's tissue, and the detected light may no longer relate in the same way to a physiological constituent. Because detected light unrelated to a physiological constituent may result in measurement inaccuracies, it may be desirable to provide a mechanism for indicating that sensor is not in sufficient contact with the patient's tissue.

SUMMARY

Certain aspects commensurate in scope with the originally claimed invention are set forth below. It should be understood that these aspects are presented merely to provide the reader with a brief summary of certain forms that the invention might take and that these aspects are not intended to limit the scope of the invention. Indeed, the invention may encompass a variety of aspects that may not be set forth below.

There is provided a sensor that includes: a sensor body; an emitter and a detector disposed adjacent the sensor body; and an electrode tissue contact sensor disposed adjacent the sensor body, wherein the electrode tissue contact sensor is capable of providing a signal related to the distance from the electrode to tissue of a patient.

There is also provided a sensor that includes: a sensor body; an emitter and a detector disposed adjacent the sensor body; and a temperature-based tissue contact sensor disposed adjacent the sensor body, wherein the temperature-based tissue contact sensor is capable of providing an electrical feedback signal related to distance between the temperature-based tissue contact sensor and tissue of a patient.

There is also provided a sensor that includes: a sensor body; and an emitter disposed adjacent the sensor body, wherein the emitter is capable of emitting a reference wavelength strongly absorbed by tissue of a patient, and a signal wavelength utilized to detect a tissue constituent; and a detector capable of detecting the reference wavelength and the signal wavelength.

BRIEF DESCRIPTION OF THE DRAWINGS

Aspects of embodiments may become apparent upon reading the following detailed description and upon reference to the drawings in which.

DETAILED DESCRIPTION

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In an embodiment, medical sensors for pulse oximetry or other applications utilizing spectrophotometry may be provided which may provide a signal related to a "sensor on" and/or a "sensor off" state. In an embodiment, the sensors may include one or more tissue contact sensors. Such sensors may provide a signal to a downstream medical device in order to convey a change in sensor status medical device and to a healthcare practitioner, for example when a sensor falls off of a patient or moves relative to a patient's tissue. Further, embodiments of such sensors may be capable of providing information as to proper sensor application. By providing information related to the correct placement of a sensor, sensors as provided herein may reduce measurement errors which may result from a sensor being located too far from the tissue to provide accurate measurements, as well as other inadequate sensor placement.

Figure 1:
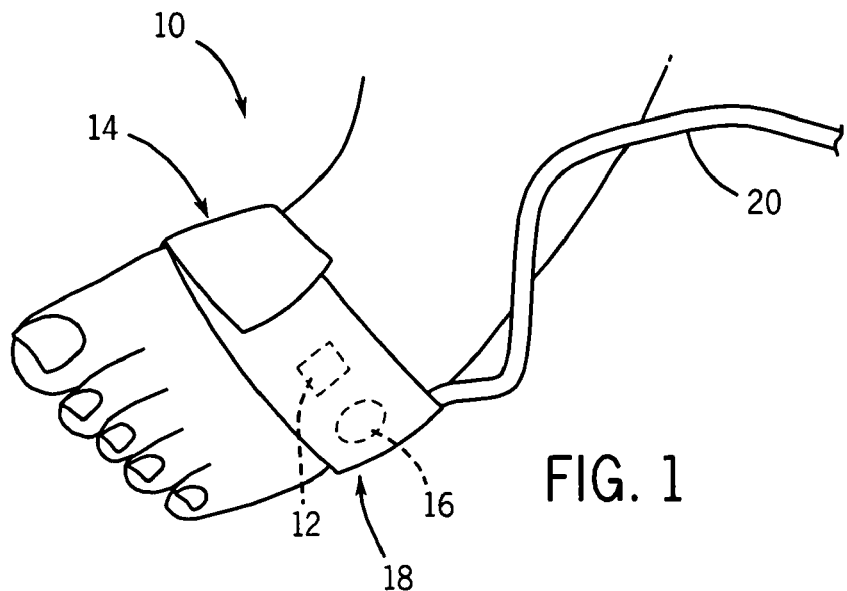
FIG. 1 illustrates a perspective view of bandage-style medical sensor including a contact sensor, according to an embodiment.

FIG. 1 shows an embodiment of a sensor 10 with a generic contact sensor 12 disposed generally adjacent and/or on a sensor body 14. As depicted in this embodiment, the sensor 10 may have a bandage-style sensor body 14, capable of conforming to a patient's foot. In an embodiment, the sensor 10 includes an emitter 16 and a detector 18. The signal from the detector 18 and the signal from the contact sensor 12 may be sent via sensor cable 20 to a downstream medical device discussed in more detail below. It should also be understood that the contact sensor 12 may be a separate assembly disposed generally adjacent and/or on the sensor body 14, or may be integral with the sensor circuit connected to the emitter 16 and the detector 18. In an embodiment, a mechanical switch contact sensor, such has those provided herein, may be electrically in series with the emitter 16. A closing or opening of a circuit may control power to the emitter 16 or the detector 18.

In an embodiment, the contact sensor 12 may be used with any suitable sensor type, including reusable and/or disposable sensors, as well as clip-on or bandage-style sensors, among others. Further, it should be understood that the contact sensor 12 may be used with sensors applied to any suitable tissue site (e.g., finger, ear, toe, forehead). The contact sensor 12 may be disposed on the sensor body 14 in any suitable location. As depicted in this embodiment, the contact sensor 12 may be proximate to the emitter 16. In transmission-type sensors 10 in which the emitter 16 and the detector 18 are positioned across the tissue from one another, it may be advantageous to position the contact sensor 12 away from the area between the emitter 16 and the detector 18. In this case, the contact sensor 12 may not be located in an area of the sensor body 14 that may fold around the tissue and thus may not conform closely enough to provide an accurate contact signal. In an embodiment, in reflectance-type sensors in which the emitter 16 and the detector 18 are side-by-side, the contact sensor 12 may be located in any suitable location on the sensor body 14.

Figure 2A:
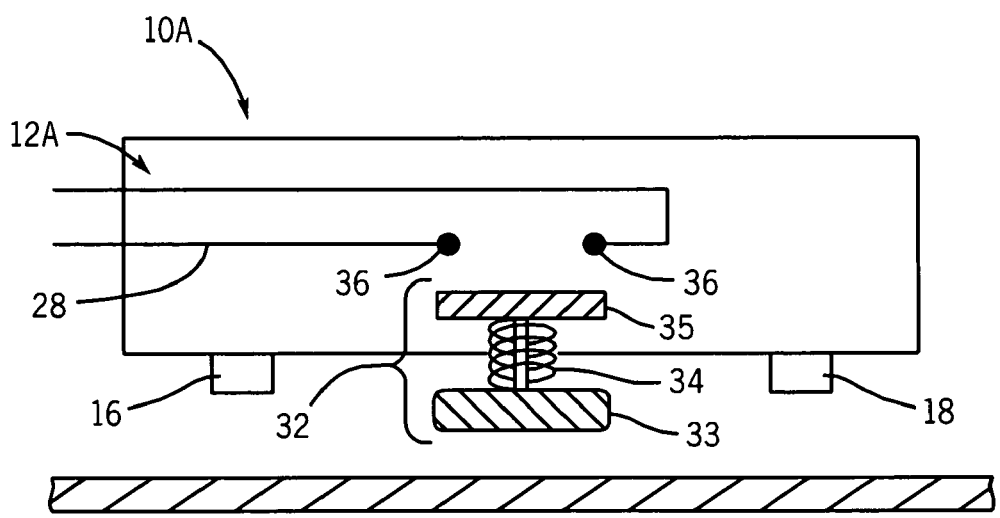
FIG. 2A is cross-sectional view of a medical sensor including a plunger-activated mechanical contact sensor, according to an embodiment.
Figure 2B:
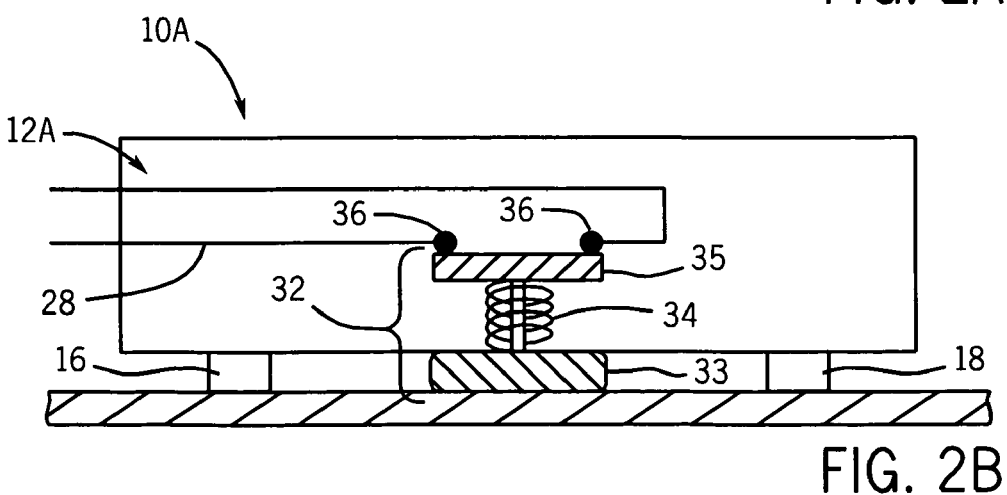
FIG. 2B is cross-sectional view of the sensor of FIG. 2A applied to a patient's tissue with the mechanical contact sensor engaged to close a circuit, according to an embodiment.

FIG. 2A and FIG. 2B illustrate an embodiment of a medical sensor 10A with a micro-switch contact sensor 12A. The micro-switch contact sensor 12A may be disposed on or generally adjacent to the sensor 10A in any appropriate location, such as between the emitter 16 and the detector 18, as depicted. The micro-switch contact sensor 12A may include a plunger assembly 32 which may be capable of closing a circuit 28 upon proper application of the sensor 10A to the probed tissue site.

In an embodiment, the plunger assembly 32 includes a tissue contact element 33, a biasing member 34, and a switch element 35. Generally, the switch element 35 may be formed from any suitable conductive material, such as a metal. The tissue contact element 33 may be formed from any suitable material that may be sufficiently resilient to transmit pressure from the tissue to the biasing member 34, while also being generally comfortable against a patient's tissue.

In an embodiment, suitable materials for forming the tissue contact element 33 may include thermoplastic polymers or metals, for example. The plunger assembly 32 may be biased by the biasing member, such as a spring 34, such that the switch element 35 will not close the circuit 28 without sufficient pressure being applied to the tissue contact element 33. This may result in the "resting state" of the circuit 28 being open. The open circuit may thus correspond to the "sensor off" state.

The spring 34 may be sized such that when the sensor 10A is properly applied against a monitoring site, the plunger assembly 32 will move, and the switch element 35 will close the circuit 28 across the contacts 36. In such an embodiment, the closed circuit may correspond to the "sensor on" state.

Figure 2C:
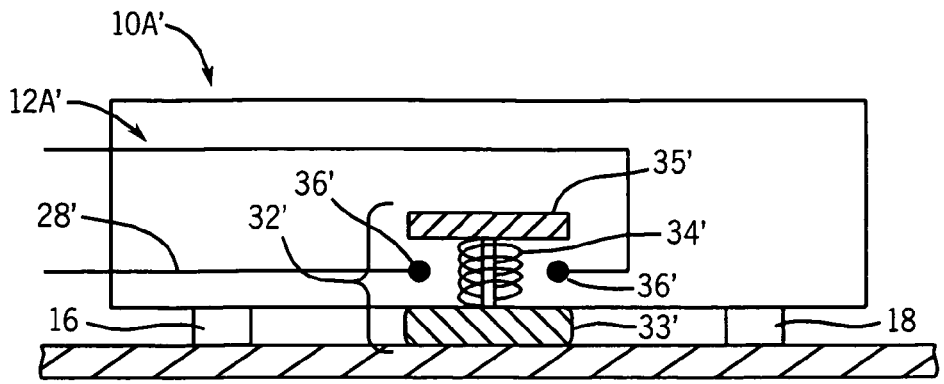
FIG. 2C shows an alternative embodiment of the sensor of FIG. 2A in which engagement of the mechanical contact sensor opens a circuit, according to an embodiment.

In an embodiment, as depicted in FIG. 2C, the plunger assembly 32' may be biased such the resting "sensor off" state of the circuit 28' is closed, and the application of force from the sensor 10A being applied to the tissue results in the switch element 35' moving to open the circuit 28'. In such an embodiment, the open circuit may correspond to the "sensor on" state.

The spring-based contact sensor 12A may provide the advantage of design flexibility as the biasing member 34 may be sized for any suitable force or pressure specification, depending on the configuration of the sensor 10A and the sensing site. Further, since the spring 34 may be configured to move only after a threshold force has been applied, the use of a spring 34 may prevent false positive "sensor on" states from incidental contact with the sensor 10A. In one embodiment, the pressure range that may be used with the spring 34 in order to close the circuit 28 may be higher than typical venous pressure (e.g., 3-5 mm Hg) and lower than typical capillary pressure (e.g., 22 mm Hg). For example, the pressure may generally be between 15 mm Hg and 20 mm Hg in an adult patient.

Figure 3A:
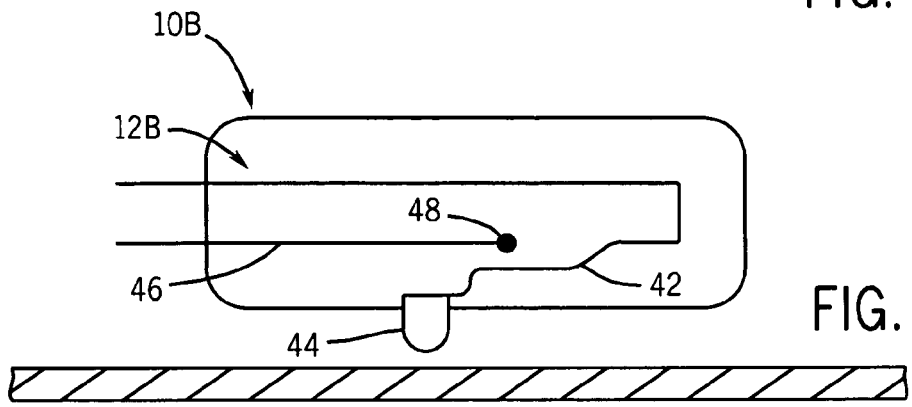
FIG. 3A is cross-sectional view of a medical sensor including an alternative mechanical contact sensor, according to an embodiment.
Figure 3B:
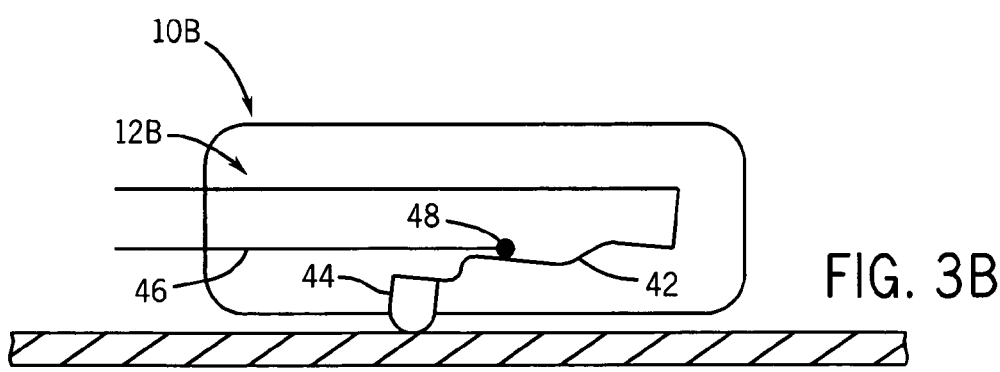
FIG. 3B is cross-sectional view of the sensor of FIG. 3A applied to a patient's tissue with the mechanical contact sensor engaged to close a circuit, according to an embodiment.
Figure 3C:
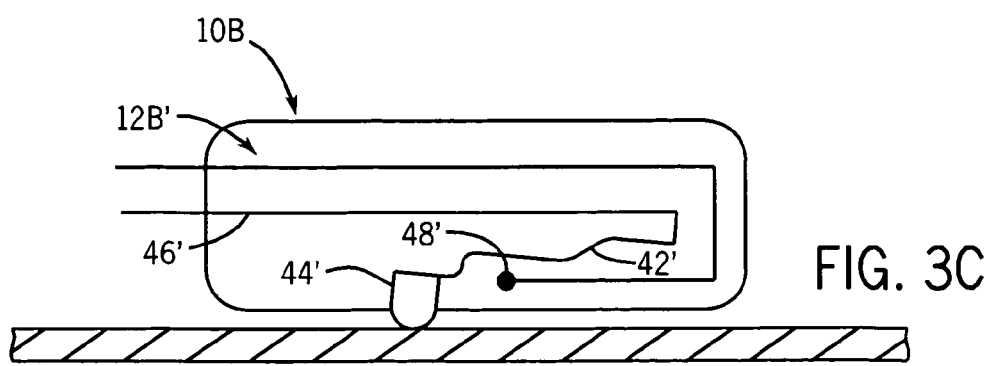
FIG. 3C shows an alternative embodiment of the sensor of FIG. 3A in which engagement of the mechanical contact sensor opens a circuit, according to an embodiment.

FIG. 3A illustrates an embodiment of a sensor 10B with a contact sensor 12B which includes a leaf spring switch 42. In an embodiment, the leaf spring switch 42 includes a tissue contact element 44 which may be capable of resting against the tissue site being probed. In an embodiment, the leaf spring switch 42 is connected to a circuit 46, such that when the sensor is in the resting "sensor off" state, the circuit 46 is open. Upon suitable pressure being applied to the leaf spring switch 42, the leaf spring switch 42 is pushed against the contact 48, causing the circuit 46 to close, resulting in a signal which may indicate that the sensor is in the "sensor on" state, as shown in FIG. 3B. Thus, the portion of the leaf spring switch 42 that closes the circuit may be formed from a suitably conductive material. In an embodiment, such a contact sensor 12B may be relatively simple in design and configuration, and lightweight. This may enable certain cost and manufacturing advantages. In an alternative embodiment, shown in FIG. 3C, the leaf spring switch 42' of the contact sensor 12B' may be biased so that the resting "sensor off" state is a closed circuit 46'. When the sensor is in close contact with the skin, the leaf spring switch 42' is pushed up, resulting in an open circuit indicating the "sensor on" state.

Figure 4:
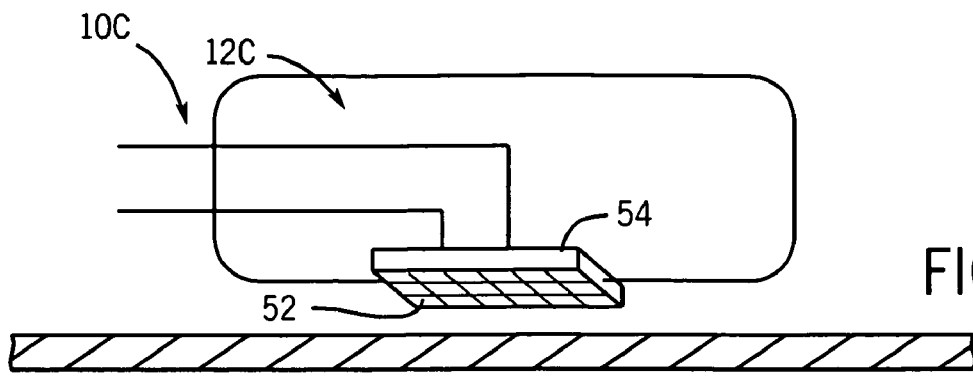
FIG. 4 illustrates an exemplary strain-gauge semiconductor contact sensor, according to an embodiment.

FIG. 4 shows an embodiment of a sensor 10C with a strain gauge contact sensor 12C. The strain gauge contact sensor 12C may incorporate a conductive grid 52 applied to a carrier matrix 54, for example a semiconductive material, that is capable of relaying a signal related to a pressure level when the sensor 10C is properly applied at a sensing site. In an embodiment, the electrical resistance of the grid may vary linearly with strain, and force or pressure on the strain gauge contact sensor 12C may be determined by measuring the change in resistance. Such a configuration may provide the advantage of relaying more detailed information about the nature of the contact rather than only an on/off signal. A downstream medical device such as a monitor, discussed below, may process the signal in order to characterize the nature of the pressure and determine if the pressure is associated with a "sensor on" or "sensor off" state, among other determinations utilizing the signal.

Figure 5A:
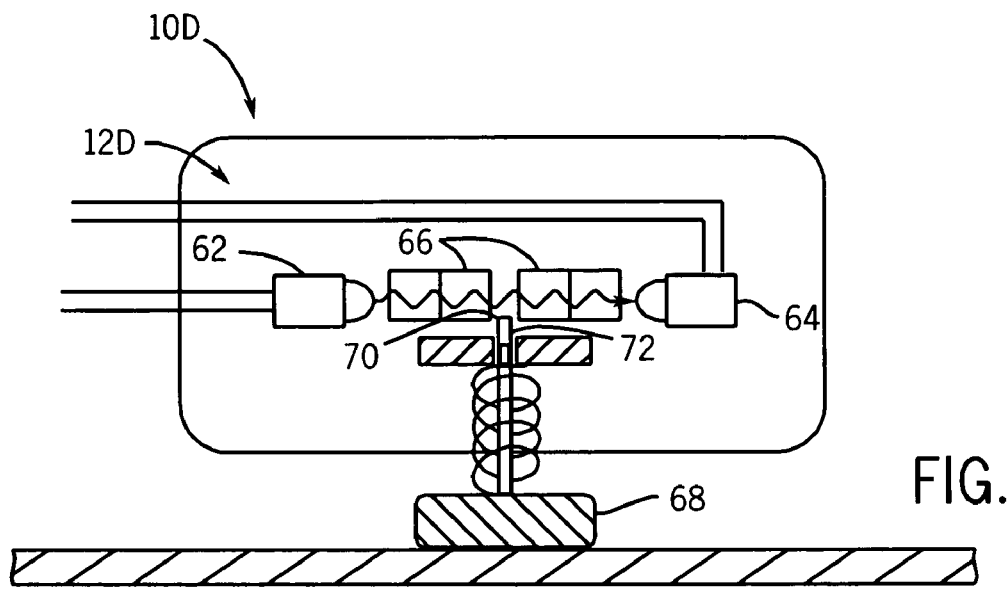
FIG. 5A illustrates an exemplary optical-type contact sensor including a mechanical plunger, according to an embodiment.
Figure 5B:
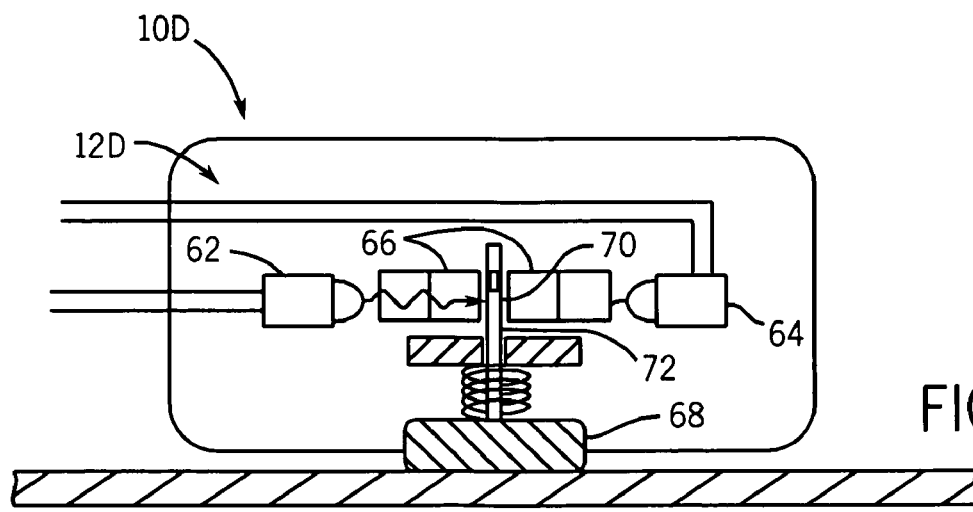
FIG. 5B is a view of the sensor of FIG. 5A applied to a patient's tissue with the optical contact blocked, according to an embodiment.

FIGS. 5A and 5B illustrate an embodiment of a sensor 10D, which may include a contact sensor 12D in which a mechanical switch may affect an optical component. In such an embodiment, a mechanical component may move within an optical path to block light from reaching a detector, or may move generally out of an optical path to allow light to reach a detector. Thus, the contact sensor 12D may relay a signal related to detected light as an indication of whether the sensor 10D is properly applied to the tissue. In addition to an emitter 16 and detector 18 (not shown) which are related to the physiological signal sensing function of the sensor 10D, the sensor 10D may also include additional optical components that are part of the contact sensor 12D.

As depicted in the embodiment in FIG. 5, the contact sensor 12D may include a secondary emitter 62 and a secondary detector 64 which are generally in-line with apertures 66 along their optical path. In an embodiment, a spring-biased plunger assembly 68 may be configured to block light or allow light to reach the secondary detector 64, depending on whether pressure is being applied to the spring biased plunger assembly 68.

The spring-biased plunger assembly 68 may move a predetermined amount upon proper application of the sensor 10D to a tissue site. The application of the sensor 10D may transmit a force to the spring-biased plunger assembly 68 which may move a shutter 70 generally out of line with the optical path between the secondary emitter 62 and the secondary detector 64, which may inhibit and/or prevent emitted light from impinging the secondary detector 64, as shown in FIG. 5B. In an embodiment, the secondary emitter 62 and the secondary detector 64 may be operatively connected to a downstream medical device, which may process the contact sensor 12D signal. Thus, the "sensor on" signal may be related to a decrease in light detected by the secondary detector 64.

In an embodiment, the shutter 70 may be positioned along the spring biased plunger assembly 68 such that the application of pressure to the contact sensor 12D may move the shutter 70 generally in-line with the optical path, and thus the "sensor on" signal may be related to an increase in detected light. In any embodiment, the shutter 70 may be positioned along a movable rod 72 which is part of the spring biased plunger assembly 68. Generally, the rod 72 may be formed from or be covered with a light absorbing material that may effectively block all or part of the light along the optical path. The shutter 70 may be a aperture or opening in the rod 72 which is suitably sized and shaped to allow some, or most of the light from the secondary emitter 62 to pass through to the detector 64.

Figure 6A:
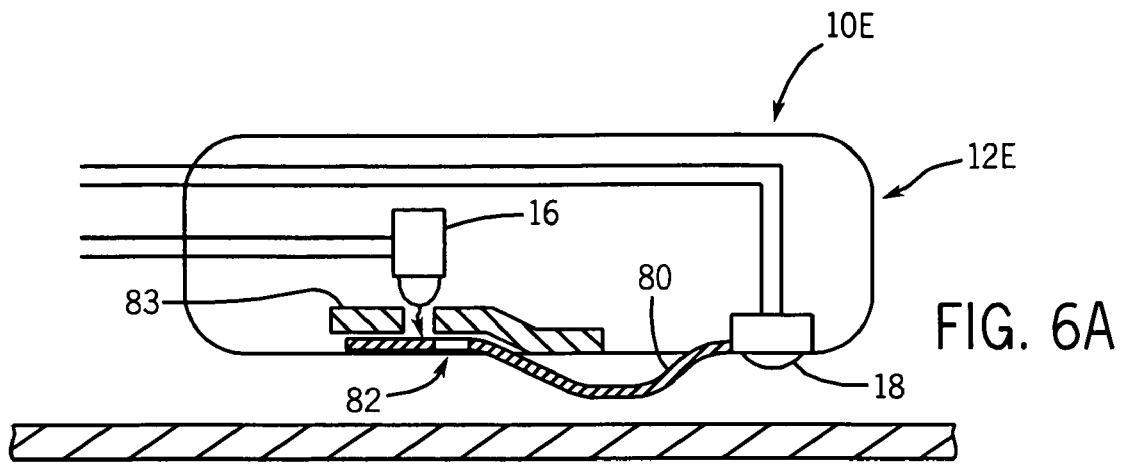
FIG. 6A illustrates an alternative optical-type contact sensor, according to an embodiment.
Figure 6B:
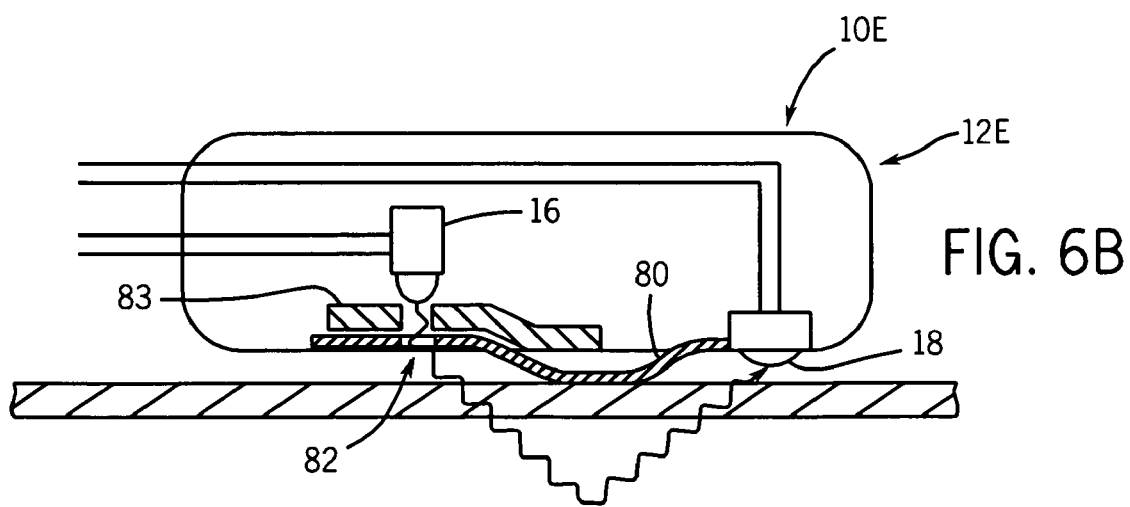
FIG. 6B is a view of the sensor of FIG. 6A applied to a patient's tissue with the optical contact opened, according to an embodiment.

FIGS. 6A and 6B illustrate an embodiment of a sensor 10E in which a contact sensor 12E includes a mechanical switch which may prevent the emitter 16 from emitting light into the tissue unless the sensor 10E has been properly applied to the patient. The pressure of application of a leaf spring 80 to the tissue site may move a shutter 82, disposed adjacent or on the leaf spring 80, into position to allow light from the emitter 16 to enter the tissue and be reflected back to the detector 18. In an embodiment, an internal light barrier 83 may provide a limited optical path for the emitted light, such that it is substantially directed towards the shutter 82. An absence of detection of emitted light may indicate to a downstream medical device as a "sensor off" condition. Such a configuration may provide the advantage of a streamlined contact sensor which is incorporated into, and provides physical feedback to, the physiological sensing components. However, such an arrangement may not allow a downstream medical device to differentiate between a nonfunctional emitter 16 and a "sensor off" condition. In such an embodiment, the downstream monitor may run a test program to check the condition emitter 16.

Figure 7A:
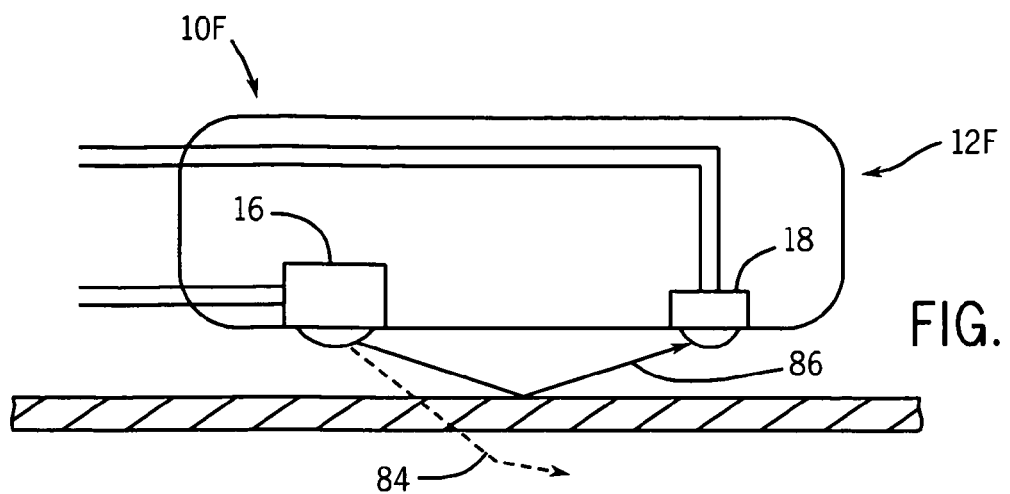
FIG. 7A illustrates an alternative optical-type contact sensor in which the sensor's emitter emits a "sensor-off" wavelength that may be detected when the sensor is not in generally adequate contact with the tissue, according to an embodiment.
Figure 7B:
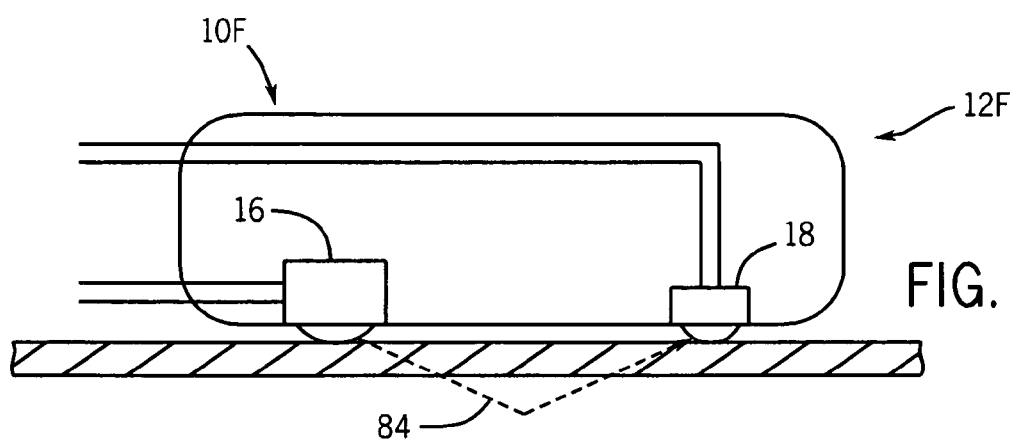
FIG. 7B is a view of the sensor of FIG. 7A applied to a patient's tissue in which the sensor's contact with the skin blocks the "sensor-off" wavelength, according to an embodiment.

In an embodiment, as shown in FIGS. 7A and 7B, a sensor 10F may include a contact sensor 12F. Contact sensor 12F may be capable of relaying an optical signal related to sensor contact utilizing particular emitted wavelengths which may be associated with a "sensor off" condition. In an embodiment, such wavelengths may be distinct from the wavelengths used to detect the physiological constituent. The wavelengths related to the "sensor off" condition may be generally strongly absorbed by the tissue, while the physiological constituent wavelengths may be generally not strongly absorbed by the tissue.

The emitter 16 may be configured to emit multiple wavelengths of light. In an embodiment, a first wavelength, as shown by dashed arrow 84, may be related to a physiological constituent. A second wavelength, as shown by solid arrow 86, may be strongly absorbed by a patient's tissue. If the sensor is not properly applied to the tissue, as shown in FIG. 7A, light of the second wavelength 86 may not be absorbed by the tissue, and may impinge the detector 18. If the sensor 10F is properly applied to the patient's tissue, light of the second wavelength 86 may be substantially absorbed by the patient's tissue, and may not impinge the detector. Furthermore, light related to the physiological constituent may properly pass through the tissue to impinge the detector 18. Thus, the "sensor off" condition may be related to an increase in light of the second wavelength 86 impinging the detector 18.

In this embodiment, such a configuration may not employ any additional mechanical components, and thus may provide manufacturing advantages. The wavelengths related to the "sensor off" condition may be selected based on the optical absorption properties of the tissue and the distance between the emitter 16 and the detector 18, among other considerations. For a pulse oximetry sensor having an emitter-detector spacing of at least a few millimeters, such a wavelength may be selected to be generally longer than about 1200 nm, so as to generally be strongly absorbed by water in the tissue, or shorter than about 600 nm, so as to be generally strongly absorbed by hemoglobin in the blood perfusing the tissue.

Figure 8:
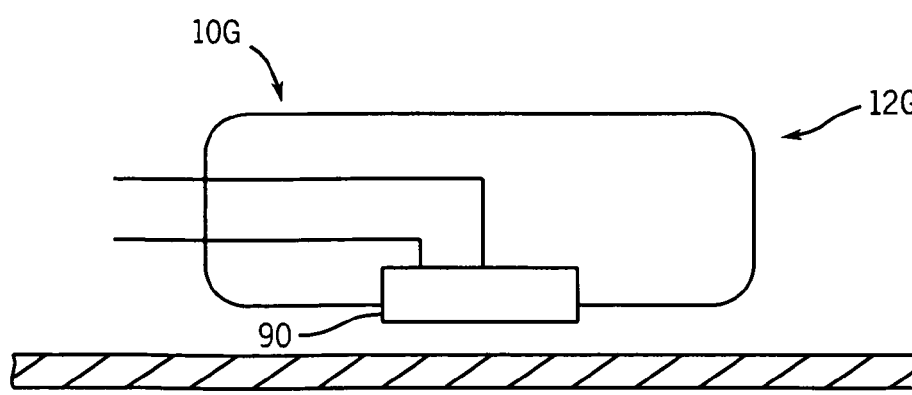
FIG. 8 illustrates an exemplary temperature contact sensor, according to an embodiment.

FIG. 8 illustrates an embodiment of a sensor 10G, in which the contact sensor 12G employs one or more temperature sensors to relay a signal related to tissue contact. The temperature sensor 90 (such as a thermistor) may be capable of measuring the temperature of the tissue site being probed. The temperature sensor 90 may provide a temperature signal which may be processed by a downstream medical device, and compared against a threshold value, such as ambient temperature, to provide an indication of a "sensor off" condition. In an embodiment, a measured temperature may be compared to a clinically determined average skin surface temperature. A significantly lower temperature measurement may indicate a "sensor off" state. In an embodiment, the contact sensor 12G of the sensor 10G may employ a plurality of temperature sensors 90 to provide additional temperature reference points. For example, when the difference between the two temperature readings is greater than a predetermined threshold value, a downstream medical device may interpret that condition as a "sensor off."

In an embodiment, a second temperature sensor (not shown) may be positioned on a non-tissue-contacting surface to measure an ambient temperature. Accordingly, when the difference between the first and second temperature measurements is less than a predetermined threshold value downstream medical device may interpret that condition as a "sensor off." The dual temperature sensing configuration, which may be more expensive than a single temperature sensing configuration, may provide a generally more reliable measurement, which may be based at least in part upon a difference between temperature measurements.

Figure 9A:
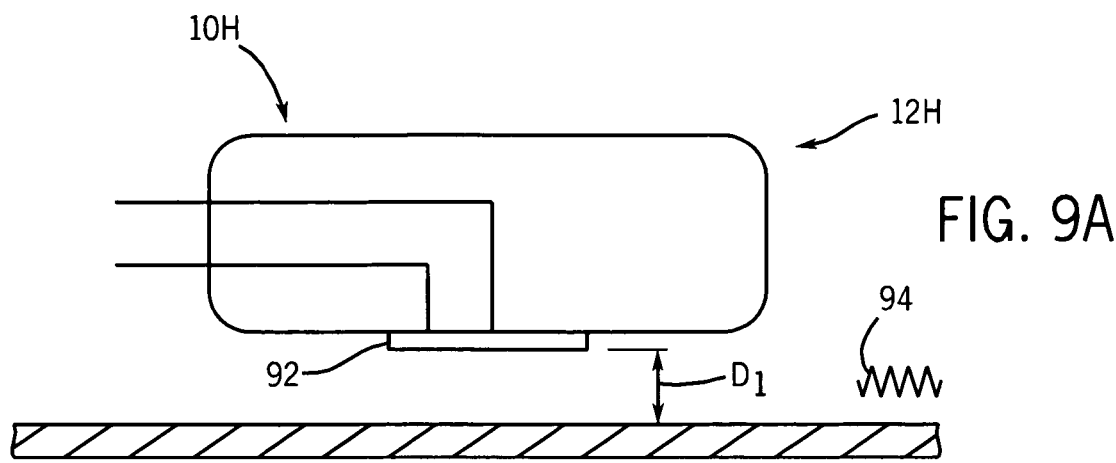
FIGS. 9A and 9B illustrate an exemplary electrode contact sensor, according to an embodiment.
Figure 9B:
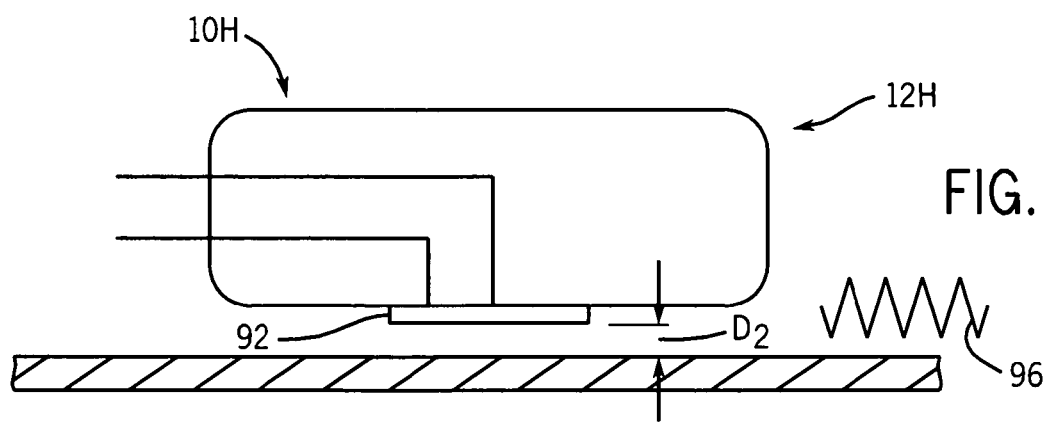

In addition to contact measurements based on mechanical switches, optical measurements, and temperature, a sensor contact with the tissue may be determined from electrical properties inherent to certain sensing components. In an embodiment, as shown in FIGS. 9A and 9B, a sensor 10H may include a contact sensor 12H having a single electrode 92 that may provide a noise signal related to the distance of the electrode 92 from the tissue. In most patient monitoring environments, electrical noise from sources such as electric lights, nearby motors, radio transmission facilities, or other nearby electrical instrumentation, is generally present. The patient's body acts, in part, as an antenna that receives these ambient noise signals. As shown in FIG. 9A, when the distance, indicated as $D_1$, from the tissue to the electrode 92 is relatively far, the electrode 92 may be in electrical-ohmic isolation from the skin and the detected noise signal, indicated by reference numeral 94, may be relatively small. As the distance between the tissue and the electrode 92 decreases, as shown in FIG. 9B, the detected noise signal, indicated by reference numeral 96, may be relatively larger. The noise signal 94 detected by the electrode 92 may be compared to a predetermined threshold corresponding with good sensor placement. For example, if the noise signal 94 is sufficiently large, the sensor 10H may be determined to be in close contact with the skin.

Such a configuration may provide cost and convenience advantages over dual electrode contact sensors that measure impedance of the skin between two electrodes. For dual electrode sensors, electrical impedance of the skin may be affected by tissue integrity and hydration as well as by the distance between the two electrodes, which may vary. As In sensor 10H a single electrode 92 relays a noise signal related to the gap between the sensor 10H and the tissue. Accordingly, the skin itself does not conduct the detected noise signal 94. Thus, the signal may not be influenced by the tissue characteristics unique to each patient. Accordingly, the sensor 10H may be more readily calibrated than dual electrode contact sensors that measure impedance of the skin between two electrodes that send a current through the skin.

Figure 10:
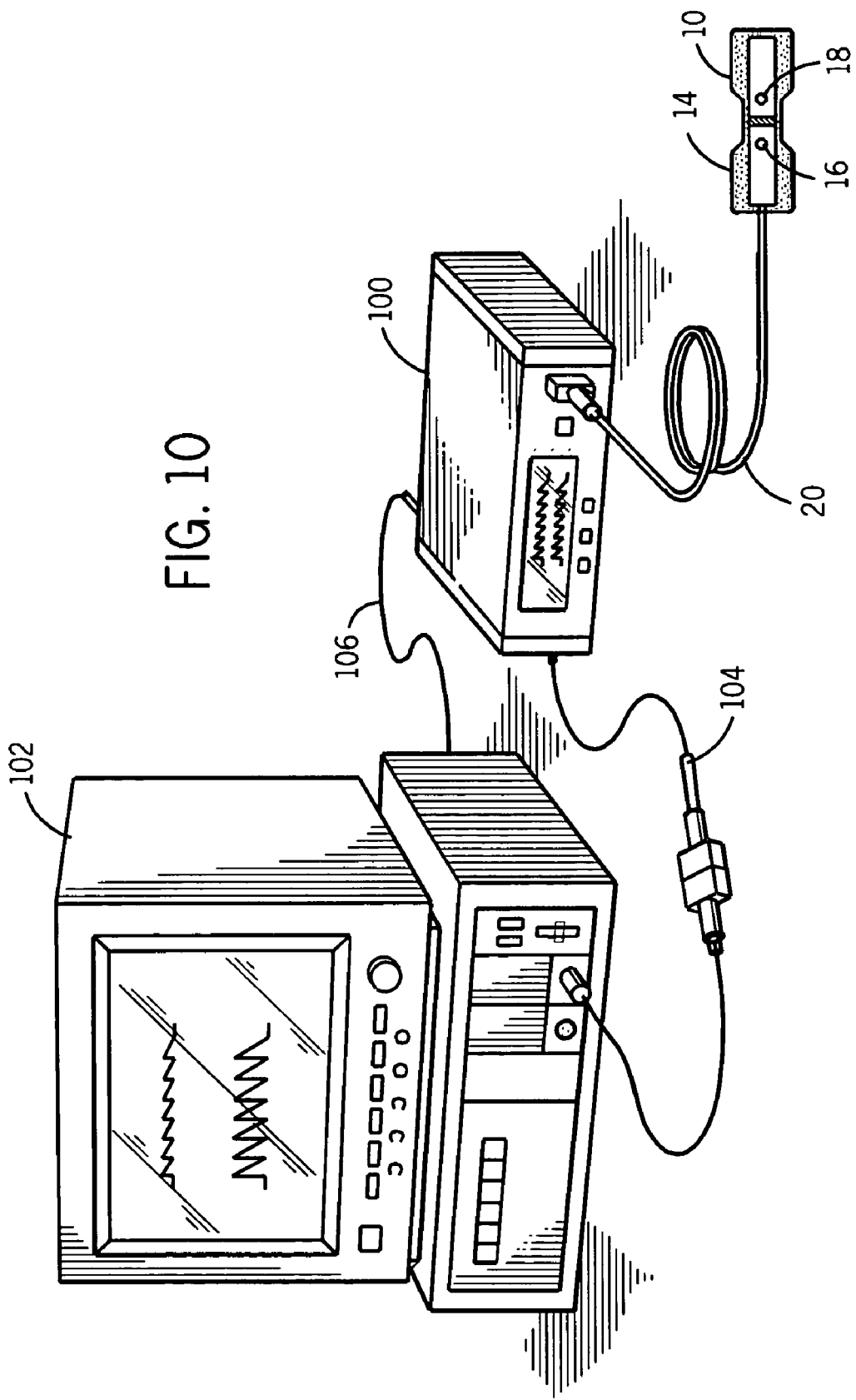
FIG. 10 illustrates a pulse oximetry system coupled to a multi-parameter patient monitor and a sensor, according to an embodiment.

In various embodiments, regardless of the type of contact sensor 12 used, a sensor, illustrated generically as a sensor 10, may be used in conjunction with a downstream medical device, which may include a pulse oximetry monitor 100, as illustrated in FIG. 10. It should be appreciated that the cable 20 of the sensor 10 may be coupled to the monitor 100 or it may be coupled to a transmission device (not shown) to facilitate wireless transmission between the sensor 10 and the monitor 100. The monitor 100 may be any suitable pulse oximeter, such as those available from Nellcor Puritan Bennett Inc. Furthermore, to upgrade conventional pulse oximetry provided by the monitor 100 to provide additional functions, the monitor 100 may be coupled to a multi-parameter patient monitor 102 via a cable or wireless connection 104 connected to a sensor input port or via a cable or wireless connection 106 connected to a digital communication port.

Figure 11:
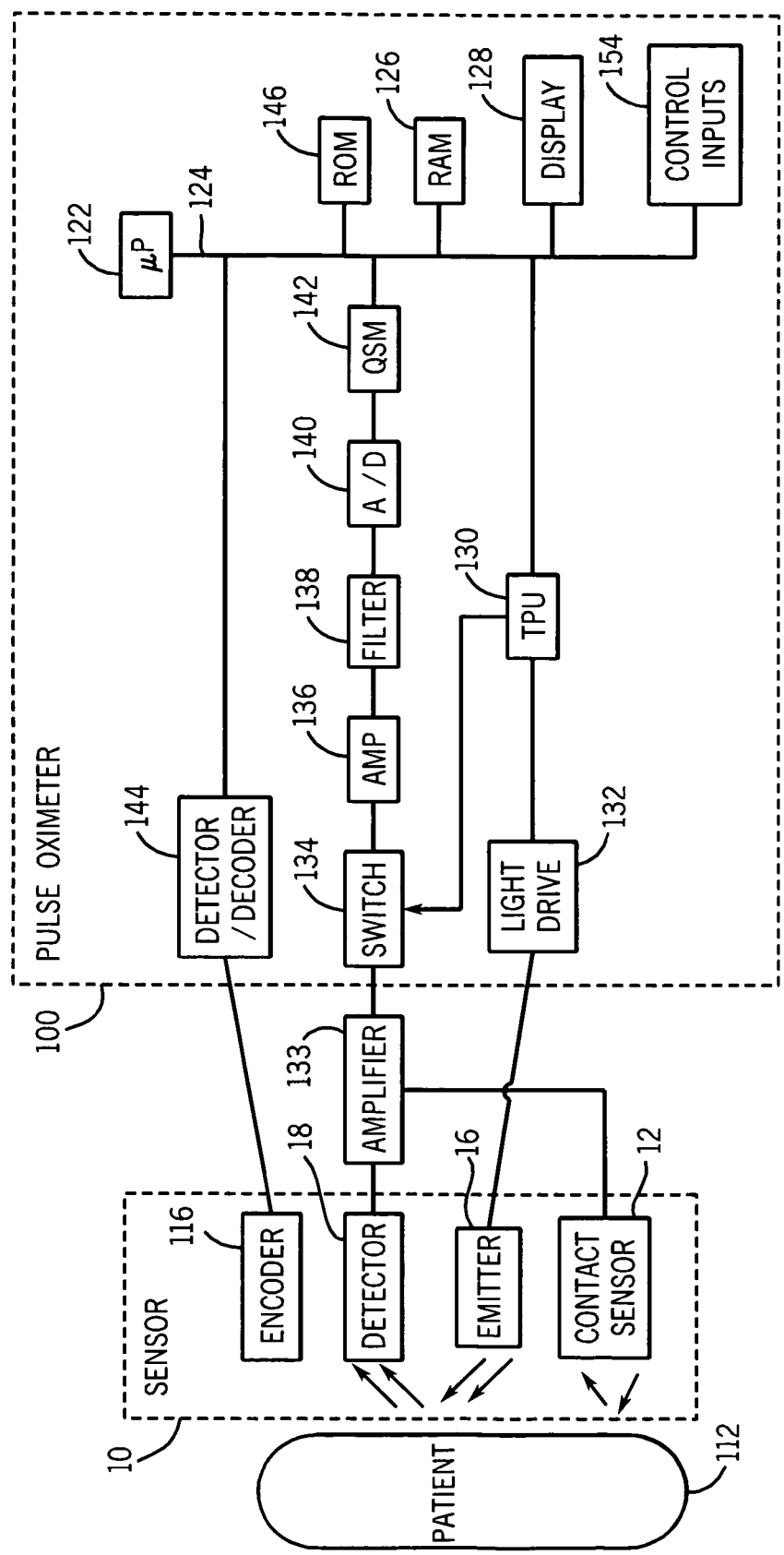
FIG. 11 is a block diagram of an exemplary pulse oximetry model connected to a sensor, according to an embodiment.

FIG. 11 is a block diagram of an embodiment of a pulse oximeter which may be configured to implement the embodiments of the present disclosure. Light from emitter 16 may pass into a blood perfused tissue 112, and may be scattered, and then detected by detector 18. A sensor 10 containing an emitter 16 and a detector 18 may also contain an encoder 116 which may be capable of providing signals indicative of the wavelength(s) of light source 16 to allow the oximeter to select appropriate calibration coefficients for calculating oxygen saturation. The encoder 116 may, in an embodiment, be a resistor. In an embodiment, the sensor 10 also includes a contact sensor 12 and may be capable of carrying a signal from the contact sensor 12 to a monitor 100.

In an embodiment, the sensor 10 may be connected to a pulse oximetry monitor 100. The monitor 100 may include a microprocessor 122 coupled to an internal bus 124. Also connected to the bus may be a RAM memory 126 and a display 128. A time processing unit (TPU) 130 may provide timing control signals to light drive circuitry 132, which controls when the emitter 16 is activated, and if multiple light sources are used, the multiplexed timing for the different light sources. TPU 130 may also control the gating-in of signals from detector 18 through an amplifier 133 and a switching circuit 134. These signals are sampled at the proper time, depending at least in part upon which of multiple light sources is activated, if multiple light sources are used. The received signal from the detector 18 and the contact sensor 12 may be passed through an amplifier 136, a low pass filter 138, and an analog-to-digital converter 140. The digital data may then be stored in a queued serial module (QSM) 142, for later downloading to RAM 126 as QSM 142 fills up. In an embodiment, there may be multiple parallel paths of separate amplifier, filter, and A/D converters for multiple light wavelengths or spectra received.

In an embodiment, the monitor 100 may be configured to receive signals from the sensor 10. The signals may be related to a physiological constituent and/or a contact sensor 12 that may be processed by the monitor 100 to indicate a sensor condition such as "sensor on" or "sensor off." The monitor 100 may be configured to provide an indication about the sensor condition, such as an audio alarm, visual alarm or a display message, such as "CHECK SENSOR." Further, the monitor 100 may be configured to receive information about the contact sensor 12 from a memory chip or other device, such as the encoder 116, which may be on the sensor 10 or the cable 20. In an embodiment, such a device may include a code or other identification parameter that may allow the monitor 100 to select an appropriate software or hardware instruction for processing the signal.

In an embodiment, a monitor 100 may run an algorithm or code for processing the signal provided by the contact sensor 12 The processing algorithm may receive information that a circuit is either opened or closed, allowing for a simple binary determination of "sensor on" or "sensor off," depending on the parameters of the particular contact sensor 12. In other embodiments, a more complex algorithm may process a signal from a primary detector 18, and/or a secondary detector, and/or other detectors, and may compare an increase or decrease in detected light to empirically-derived stored parameters to determine the sensor condition. In other embodiments, a signal may result in a hardware switch that may open or close a circuit, which may trigger the display 128 to display a sensor state message.

In an embodiment, based at least in part upon the received signals corresponding to the light received by detector 18, microprocessor 122 may calculate the oxygen saturation using various algorithms. These algorithms may require coefficients, which may be empirically determined, and may correspond to the wavelengths of light used. The algorithms may be stored in a ROM 146 and accessed and operated according to microprocessor 122 instructions.

In an embodiment of a two-wavelength system, the particular set of coefficients chosen for any pair of wavelength spectra may be determined by a value indicated by the encoder 116 corresponding to a particular light source in a particular sensor 10. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

In an embodiment, a monitor 100 may provide instructions to vary the emitter drive 132 frequency and/or pattern, and verify that the detected and de-multiplexed light signals are unaffected. Accordingly, when the sensor is receiving a significant portion of its signals from the ambient light (i.e. corresponding to a "sensor off" condition), then a change in the emitter 16 drive frequency and/or pattern will likely result in a change in the detected photocurrent and/or the de-multiplexed waveform (resulting from a change in alias frequencies). This technique may be more advantageous in a setting with sufficient ambient light.

In an embodiment, the sensor 10 includes an emitter 16 and a detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL), or other light source. The emitter 16 and detector 18 may also include optical fiber sensing elements.

In an embodiment, an emitter 16 may include a broadband or "white light" source, and the detector could include any of a variety of elements for selecting specific wavelengths, such as reflective or refractive elements or interferometers. These types of emitters and/or detectors may be coupled to the rigid or rigidified sensor via fiber optics.

In an embodiment, a sensor 10 may sense light detected from the tissue at a different wavelength from the light emitted into the tissue. Such sensors may be adapted to sense fluorescence, phosphorescence, Raman scattering, Rayleigh scattering, and/or multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other tissue constituent related metric) or a concentration of one or more biochemical components in an aqueous environment may be measured using two or more wavelengths of light. In various embodiments, these wavelengths may be infrared wavelengths between about 1,000 nm to about 2,500 nm.

It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the ultrasound, radio, microwave, millimeter wave, infrared, visible, ultraviolet, or X-ray spectra, and that any suitable wavelength of light may be appropriate for use with the present techniques.

In an embodiment, the emitter 16 and the detector 18 may be disposed on or generally adjacent to a sensor body 14, which may be made of any suitable material, such as plastic, foam, woven material, or paper. In an embodiment, the emitter 16 and the detector 18 may be remotely located and optically coupled to the sensor 10 using optical fibers. In various embodiments, the sensor 10 is coupled to a cable 20 that is responsible for transmitting electrical and/or optical signals to and from the emitter 16 and detector 18 of the sensor 10. The cable 20 may be permanently coupled to the sensor 10, or it may be removably coupled to the sensor 10—the latter alternative being more useful and cost efficient in situations where the sensor 10 is disposable.

In various embodiments, the sensor 10 may be a "transmission type" sensor. Transmission type sensors may include an emitter 16 and detector 18 that are placed on opposing sides of the sensor site. If the sensor site is a fingertip, for example, the sensor 10 is positioned over the patient's fingertip such that the emitter 16 and detector 18 lie on either side of the patient's nail bed. In other words, the sensor 10 is positioned so that the emitter 16 is located on the patient's fingernail and the detector 18 is located 180° opposite the emitter 16 on the patient's finger pad.

During operation, the emitter 16 shines one or more wavelengths of light through the patient's fingertip, and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor 10 may perform in substantially the same manner.

Reflectance type sensors also operate by emitting light into the tissue and detecting the light that is transmitted and scattered by the tissue. Reflectance type sensors may include an emitter 16 and detector 18 which are typically placed on the same side of the sensor site. For example, a reflectance type sensor may be placed on a patient's fingertip or foot such that the emitter 16 and detector 18 lie side-by-side. Reflectance type sensors detect light photons that are scattered back to the detector 18. A sensor 10 may also be a "transflectance" sensor, such as a sensor that may subtend a portion of a baby's heel.

While the resent disclosure may be capable of various modifications and alternative forms, embodiments have been shown by way of example in the drawings and have been described in detail herein. However, it should be understood that the disclosure is not intended to be limited to the particular forms disclosed. Indeed, the present techniques may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of additional blood or tissue constituents, such as carboxyhemoglobin, met-hemoglobin, total hemoglobin, intravascular dyes, and/or water content. Rather, the disclosure is to cover all modifications, equivalents, and alternatives falling within the spirit and scope of the invention as defined by the following appended claims.

What is claimed is:

1. A sensor comprising:
    a sensor body;
    an emitter and a detector disposed adjacent the sensor body;
    a temperature-based tissue contact sensor disposed adjacent the sensor body, wherein the temperature-based tissue contact sensor is configured to provide an electrical feedback signal related to distance between the temperature-based tissue contact sensor and tissue of a patient; and
    an encoder comprising stored data or code related to the temperature-based tissue contact sensor, wherein the stored data or code is configured to be read by a monitor to cause the monitor to select a set of instructions for processing the electrical feedback signal from the temperature-based tissue contact sensor and determining if the temperature-based tissue contact sensor is in contact with the tissue of the patient.

2. The sensor, as set forth in claim 1, wherein the sensor comprises a pulse oximetry sensor or a sensor configured to measure a water fraction.

3. The sensor, as set forth in claim 1, wherein the emitter comprises a light emitting diode.

4. The sensor, as set forth in claim 1, wherein the detector comprises a photodetector.

5. The sensor, as set forth in claim 1, wherein the tissue contact sensor comprises at least two temperature sensors.

6. The sensor, as set forth in claim 5, wherein the at least two temperature sensors are positioned to contact the patient.

7. The sensor, as set for in claim 5, wherein at least one of the at least two temperature sensors is configured to sense ambient temperature.

8. The sensor, as set forth in claim 5, wherein a first temperature sensor of the at least two temperature sensors is disposed adjacent the sensor body proximate to the emitter.

9. The sensor, as set forth in claim 5, wherein a first temperature sensor of the at least two temperature sensors is disposed adjacent the sensor body proximate to the detector.

10. A system comprising:
    a sensor comprising:
    a sensor body;
    an emitter and a detector disposed on the sensor body;
    a temperature-based tissue contact sensor disposed on or adjacent the sensor body, wherein the temperature-based tissue contact sensor is configured to provide a signal related to distance between the temperature-based tissue contact sensor and tissue of a patient; and
    a patient monitor operatively coupled to the sensor and the temperature-based tissue contact sensor and comprising a processor configured to receive the signal and determine if the sensor is in contact with the tissue of the patient based at least in part upon the signal from the temperature-based tissue contact sensor.

11. The system, as set forth in claim 10, wherein the processor is configured to compare the signal to a threshold and determine that the sensor is not in contact with the tissue of the patient if the signal is representative of a measured temperature that is lower than a predetermined threshold.

12. The system, as set forth in claim 11, wherein the threshold comprises a predetermined average skin surface temperature of the patient.

13. The system, as set forth in claim 10, wherein the processor is configured to compare the signal to a threshold and determine that the sensor is in contact with the tissue of the patient if the signal is representative of a measured temperature that is higher than a predetermined threshold comprising a predetermined average skin surface temperature of the patient.

14. A system, comprising:
    a sensor comprising:
        a sensor body;
        an emitter and a detector disposed on the sensor body; and
        a first temperature sensor disposed on a surface of the sensor body configured to contact a tissue of a patient when the sensor is applied to a patient, wherein the first temperature sensor is configured to provide a first signal; and
        a second temperature sensor disposed on a non-tissue-contacting surface of the sensor body, wherein the second temperature sensor is configured to provide a second signal; and
    a patient monitor operatively coupled to the sensor and comprising:
    an input circuit configured to receive the first signal and the second signal;
    a memory storing instructions for:
    determining a first temperature measurement based on the first signal;
    determining a second temperature measurement based on the second signal; and
    determining a sensor condition based on a difference between the first temperature measurement and the second temperature measurement; and an output circuit configured to provide an indication of the sensor condition.

15. The system, as set forth in claim 14, wherein the instructions for determining a sensor condition based on a difference between the first temperature measurement and the second temperature measurement comprise comparing the difference to a threshold.

16. The system, as set forth in claim 14, comprising a display configured to display the indication of the sensor condition.

17. The system, as set forth in claim 16, wherein the indication of the sensor condition comprises a text indication.

18. The system, as set forth in claim 16, wherein the indication of the sensor condition comprises an alarm.

* * * * *